US010694931B2

(12) United States Patent
Urakawa et al.

(10) Patent No.: US 10,694,931 B2
(45) Date of Patent: Jun. 30, 2020

(54) ENDOSCOPE SYSTEM THAT MEASURES AMPLITUDE OF SIGNAL TO DETERMINE STATE OF TRANSMISSION IN ORDER TO ADJUST VOLTAGE OF POWER SUPPLY

(71) Applicant: OLYMPUS CORPORATION, Tokyo (JP)

(72) Inventors: Tsutomu Urakawa, Hachioji (JP); Susumu Kawata, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/209,094

(22) Filed: Dec. 4, 2018

(65) Prior Publication Data
US 2019/0110676 A1 Apr. 18, 2019

Related U.S. Application Data

(63) Continuation of application No. PCT/JP2017/007730, filed on Feb. 28, 2017.

(30) Foreign Application Priority Data

Jul. 29, 2016 (JP) ................................. 2016-150314

(51) Int. Cl.
A61B 1/00 (2006.01)
A61B 1/04 (2006.01)
(Continued)

(52) U.S. Cl.
CPC .......... *A61B 1/128* (2013.01); *A61B 1/00009* (2013.01); *A61B 1/00013* (2013.01);
(Continued)

(58) Field of Classification Search
CPC ..... A61B 1/128; A61B 1/045; A61B 1/00117; A61B 1/00045; A61B 1/00025;
(Continued)

(56) References Cited

U.S. PATENT DOCUMENTS 7,391,800 B2 * 6/2008 Takahashi .............. B82Y 20/00
372/43.01
2006/0171437 A1 8/2006 Takahashi
(Continued)

FOREIGN PATENT DOCUMENTS

JP S61-121590 A 6/1986
JP 2006-095330 A 4/2006
(Continued)

OTHER PUBLICATIONS

International Search Report dated May 23, 2017 issued in PCT/JP2017/007730.

*Primary Examiner* — Susan E. Hodges
(74) *Attorney, Agent, or Firm* — Scully, Scott, Murphy & Presser, P.C.

(57) ABSTRACT

An endoscope includes an optical transmission module configured to convert each of the image pickup signal and the test signal into an optical signal and output the optical signal, and a signal amplitude measuring section configured to add signal amplitude information to the image pickup signal and the test signal, and a video processor includes an optical reception module configured to receive the optical signals and convert each of the optical signals into an electric signal and output the electric signal, an information acquiring section configured to acquire transmission information on each of the optical signals, the transmission information including the signal amplitude information, a determination section configured to determine a state of transmission of the optical signal, and a power supply adjusting section configured to adjust the applied voltage for the optical transmission module according to a result of the determination and output the applied voltage.

7 Claims, 18 Drawing Sheets

(51) Int. Cl.

| | |
|---|---|
| *H04N 5/30* | (2006.01) |
| *H04N 5/374* | (2011.01) |
| *H04N 5/66* | (2006.01) |
| *G02B 23/24* | (2006.01) |
| *A61B 1/12* | (2006.01) |
| *A61B 1/045* | (2006.01) |
| *H04N 17/00* | (2006.01) |
| *G02B 23/26* | (2006.01) |
| *H04N 5/225* | (2006.01) |

(52) U.S. Cl.
CPC ...... *A61B 1/00025* (2013.01); *A61B 1/00045* (2013.01); *A61B 1/00117* (2013.01); *A61B 1/04* (2013.01); *A61B 1/045* (2013.01); *G02B 23/24* (2013.01); *G02B 23/2484* (2013.01); *G02B 23/26* (2013.01); *H04N 5/30* (2013.01); *H04N 5/3741* (2013.01); *H04N 5/66* (2013.01); *H04N 17/002* (2013.01); *H04N 2005/2255* (2013.01)

(58) Field of Classification Search
CPC ... A61B 1/00013; A61B 1/00009; A61B 1/04; H04N 17/002; H04N 5/66; H04N 5/3741; H04N 5/30; H04N 2005/2255; G02B 23/24; G02B 23/26; G02B 23/2484
USPC .......................................................... 348/65
See application file for complete search history.

(56) References Cited

U.S. PATENT DOCUMENTS

| | | | |
|---|---|---|---|
| 2009/0058997 | A1 | 3/2009 | Kato |
| 2015/0209035 | A1* | 7/2015 | Zemlok ............... G01D 18/008 73/1.01 |
| 2015/0297070 | A1* | 10/2015 | Ide ....................... A61B 1/0008 600/103 |
| 2016/0206185 | A1 | 7/2016 | Kinouchi |
| 2017/0258298 | A1* | 9/2017 | Urakawa .............. G02B 23/24 |

FOREIGN PATENT DOCUMENTS

| | | |
|---|---|---|
| JP | 2006-245473 A | 9/2006 |
| JP | 2007-260066 A | 10/2007 |
| JP | 2009-061032 A | 3/2009 |
| JP | 2010-051503 A | 3/2010 |
| WO | WO 2014/196287 A1 | 12/2014 |
| WO | WO 2016/002415 A1 | 1/2016 |
| WO | WO 2016/117165 A1 | 7/2016 |

\* cited by examiner

FIG. 5

| PATTERN | 1 | 2 | 3 | 4 | 5 | 6 | 7 | 8 |
|---|---|---|---|---|---|---|---|---|
| LIGHT AMOUNT | × | ○ | × | × | × | ○ | ○ | ○ |
| BER | ○ | × | × | ○ | × | × | ○ | ○ |
| AMPLITUDE | ○ | ○ | ○ | × | × | × | × | ○ |
| PROCESSING | INCREASE POWER SUPPLY VOLTAGE | | | DECREASE POWER SUPPLY VOLTAGE | | | MAKE SWITCH TO IMAGE PICKUP SIGNAL + PROVIDE ERROR DISPLAY | MAKE SWITCH TO IMAGE PICKUP SIGNAL |

| PATTERN | 1 | 2 | 3 | 4 |
|---|---|---|---|---|
| LIGHT AMOUNT | × | × | ○ | ○ |
| BER | ○ | × | × | ○ |
| PROCESSING | | INCREASE POWER SUPPLY VOLTAGE | MAKE SWITCH TO IMAGE PICKUP SIGNAL | |

| PATTERN | 1 | 2 |
|---|---|---|
| LIGHT AMOUNT | × | ○ |
| PROCESSING | INCREASE POWER SUPPLY VOLTAGE | MAKE SWITCH TO IMAGE PICKUP SIGNAL |

| PATTERN | 1 | 2 |
|---|---|---|
| BER | × | ○ |
| PROCESSING | INCREASE POWER SUPPLY VOLTAGE | MAKE SWITCH TO IMAGE PICKUP SIGNAL |

FIG. 21

| PATTERN | 1 | 2 | 3 |
|---|---|---|---|
| BER | × | ○ | ○ |
| AMPLITUDE | ○ | × | ○ |
| PROCESSING | INCREASE POWER SUPPLY VOLTAGE | MAKE SWITCH TO IMAGE PICKUP SIGNAL + PROVIDE ERROR DISPLAY | MAKE SWITCH TO IMAGE PICKUP SIGNAL |

ENDOSCOPE SYSTEM THAT MEASURES AMPLITUDE OF SIGNAL TO DETERMINE STATE OF TRANSMISSION IN ORDER TO ADJUST VOLTAGE OF POWER SUPPLY

CROSS REFERENCE TO RELATED APPLICATION

This application is a continuation application of PCT/JP2017/007730 filed on Feb. 28, 2017 and claims benefit of Japanese Application No. 2016-150314 filed in Japan on Jul. 29, 2016, the entire contents of which are incorporated herein by this reference.

BACKGROUND OF THE INVENTION

1. Field of the Invention

The present invention relates to an endoscope system and specifically relates to an endoscope system in which a signal outputted from an image pickup device is transmitted using optical fibers.

2. Description of the Related Art

Endoscope systems each including, e.g., an endoscope configured to pick up an image of an object inside a subject and an image processing apparatus (signal processing apparatus) configured to generate an observation image of the object picked up by the endoscope have widely been used in the medical field, the industrial field, etc.

As the endoscope in such an endoscope system as above, an endoscope employing an image pickup device to be driven by a predetermined clock signal and including a signal transmission cable disposed inside, the cable being configured to transmit an image pickup signal outputted from the image pickup device, has conventionally been known.

Here, in recent years, an example in which as an image pickup device in an endoscope, a CMOS (complementary metal-oxide semiconductor) image sensor is employed has been proposed (Japanese Patent Application Laid-Open Publication No. 2006-095330).

Also, for this type of CMOS image sensor, an example in which the CMOS image sensor itself includes what is called an AFE (analog front-end) and performs predetermined A/D conversion to output an image pickup signal that is a digital signal has been known.

On the other hand, as a signal transmission cable configured to transmit an image pickup signal outputted from an image pickup device disposed in an endoscope, for example, as described in Japanese Patent Application Laid-Open Publication No. 61-121590, a configuration in which an image pickup signal outputted from an image pickup unit including an image pickup device is transmitted using a predetermined metal lead wire has widely been known.

On the other hand, in recent years, as a signaling method for transmitting an image pickup signal outputted from an image pickup block, an optical signal transmission method using optical fiber connection such as indicated in Japanese Patent Application Laid-Open Publication No. 2007-260066 has been proposed.

In an optical signal transmission method in an endoscope system such as stated above, an optical transmission module is disposed in a distal end portion of an endoscope so as to convert an image pickup signal outputted from an image pickup device into an optical signal and transmit the optical signal.

SUMMARY OF THE INVENTION

An endoscope system according to an aspect of the present invention includes an endoscope configured to pick up an image of a subject, and an information processing apparatus to which the endoscope is connectable. The endoscope includes an image pickup device configured to pick up an image of the subject and output at least a predetermined first electric signal, an optical transmission module including a light emitting element configured to be driven by a predetermined applied voltage and convert the first electric signal from the image pickup device into an optical signal and output the optical signal, an optical fiber configured to transmit the optical signal outputted from the optical transmission module, and a signal amplitude measuring circuit configured to measure a signal amplitude of the first electric signal and add signal amplitude information that is a result of the measurement to the first electric signal. The information processing apparatus includes an optical reception module configured to receive the optical signal transmitted from the optical fiber and convert the optical signal into a predetermined second electric signal and output the predetermined second electric signal, and output a third electric signal according to a light amount of the optical signal, an information acquiring circuit configured to acquire transmission information relating to the optical signal, the transmission information including the signal amplitude information, based on the second electric signal outputted from the optical reception module, a determination apparatus configured to determine a transmission state of the optical signal based on the transmission information acquired by the information acquiring circuit, and a power supply adjusting circuit configured to adjust the applied voltage according to a result of the determination by the determination apparatus and output the applied voltage.

BRIEF DESCRIPTION OF THE DRAWINGS

FIG. 5 is a table indicating processing to be performed by a determination section for each of patterns related to respective pieces of information acquired by an information acquiring section in the endoscope system according to the first embodiment;

FIG. 21 is a table indicating processing performed by a determination section for each of patterns related to respective pieces of information acquired by an information acquiring section in the endoscope system according to the fourth modification of the first embodiment;

DETAILED DESCRIPTION OF THE PREFERRED EMBODIMENT(S)

Embodiments of the present invention will be described below with reference to the drawings.

First Embodiment

Figure 1:
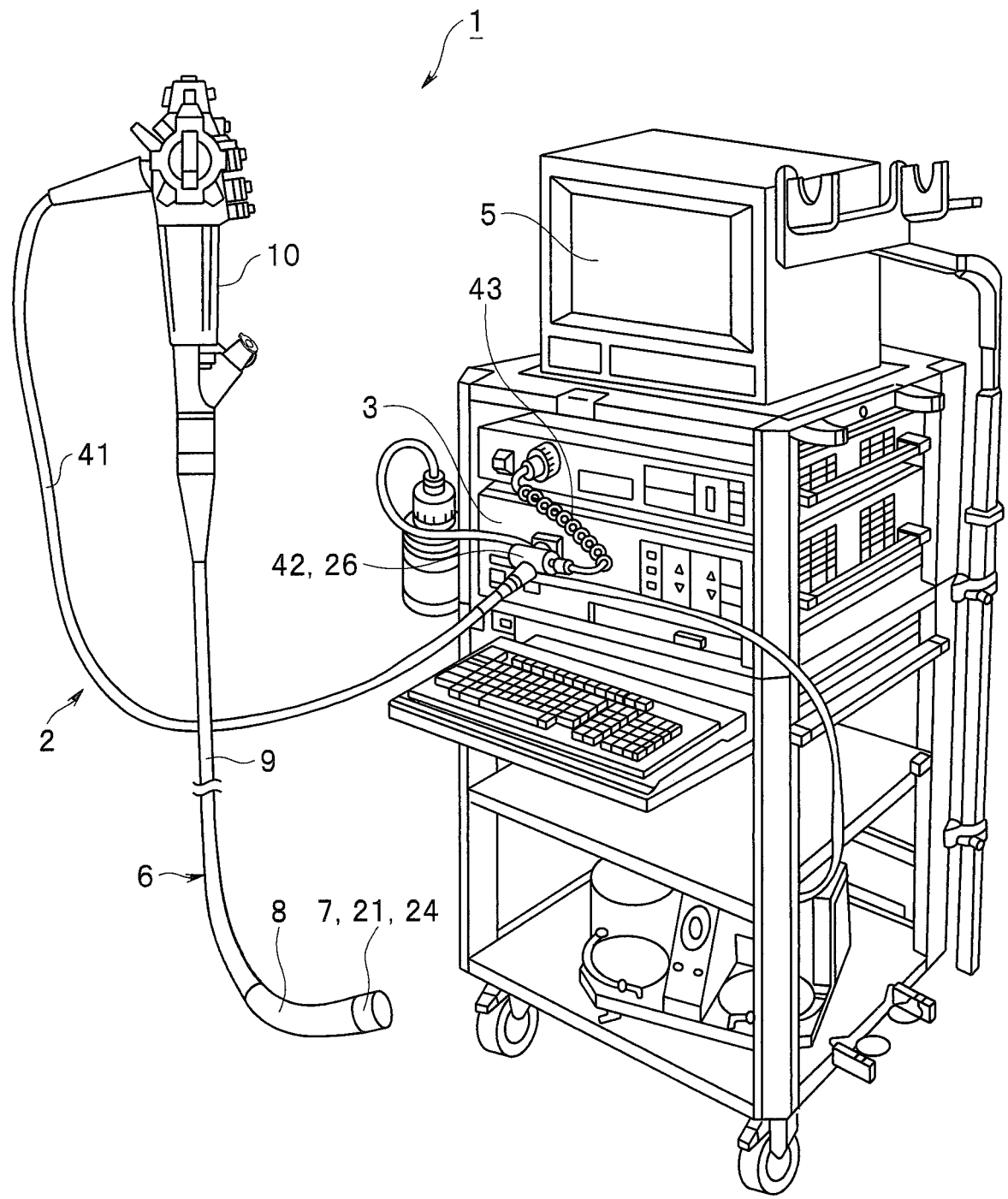
FIG. 1 is a diagram illustrating a configuration of an endoscope system according to a first embodiment of the present invention.
Figure 2:
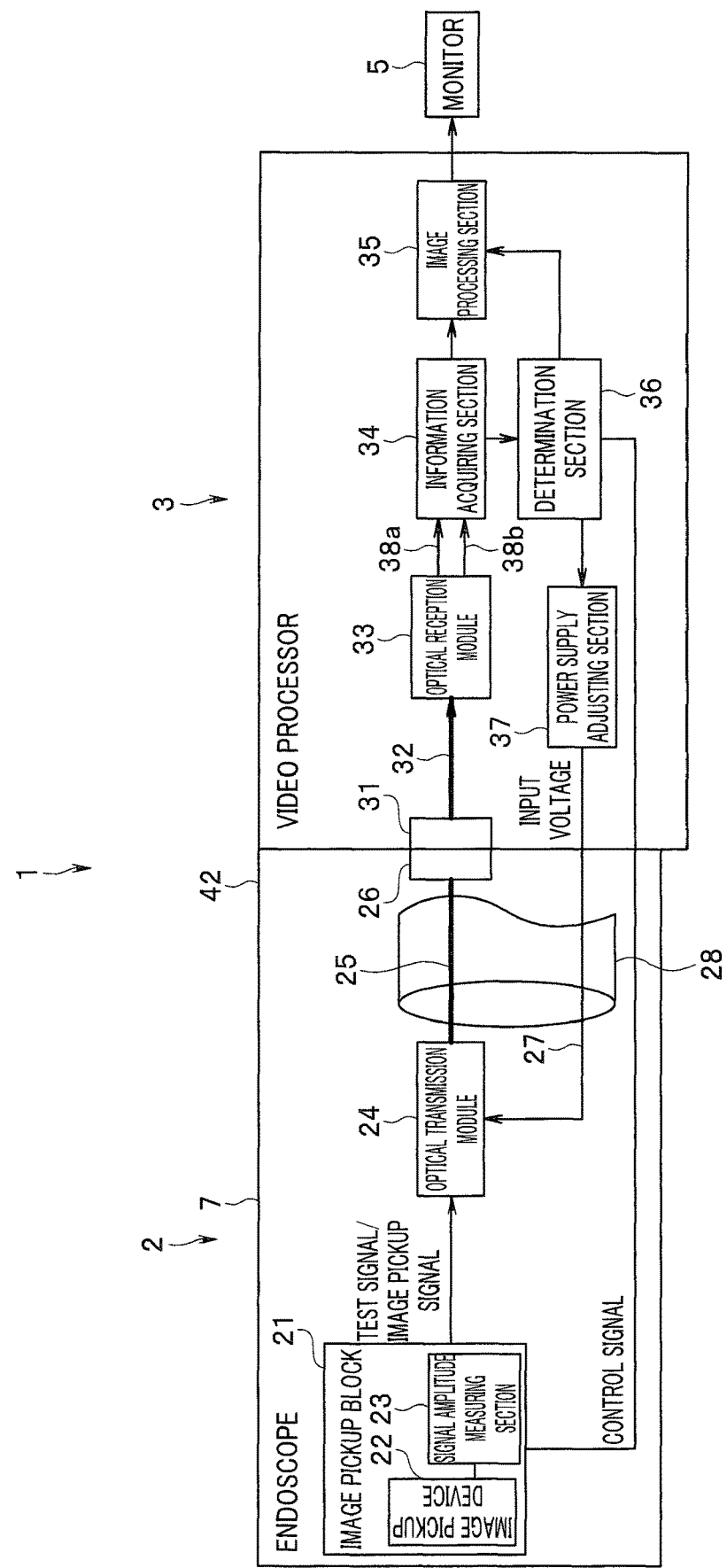
FIG. 2 is a block diagram illustrating an electric configuration of the endoscope system according to the first embodiment.

FIG. 1 is a diagram illustrating a configuration of an endoscope system according to a first embodiment of the present invention, and FIG. 2 is a block diagram illustrating an electric configuration of the endoscope system according to the first embodiment.

As illustrated in FIGS. 1 and 2, the endoscope system 1 according to the first embodiment includes: an endoscope 2 configured to allow observation of a subject and pickup an image of the subject; a video processor 3 connected to the endoscope 2, the video processor 3 being configured to function as a signal processing apparatus (information processing apparatus) that receives an input of an image pickup signal and subjects the image pickup signal to predetermined image processing and function as a light source apparatus that supplies illuminating light for illuminating the subject; and a monitor 5 as a display apparatus configured to display an observation image according to the image pickup signal.

The endoscope 2 includes an elongated insertion portion 6 to be inserted into, e.g., a body cavity of a subject, an endoscope operation section 10 disposed on the proximal end side of the insertion portion 6, the endoscope operation section 10 being to be grasped and operated by a surgeon, and a universal cord 41 including one end portion provided so as to extend from a side portion of the endoscope operation section 10.

The insertion portion 6 includes a rigid distal end portion 7 provided on the distal end side, a bendable bending portion 8 provided at a rear end of the distal end portion 7, and a flexible tube portion 9 provided at a rear end of the bending portion 8, the flexible tube portion 9 having a long length and flexibility.

A connector 42 is provided on the proximal end side of the universal cord 41 and the connector 42 is detachably connected to a front face of the video processor 3.

In the connector 42, a pipe sleeve (not illustrated), which serves as a connection end portion of a fluid conduit projecting from a distal end of the connector 42, and a light guide pipe sleeve (not illustrated), which serves as an illuminating light supply end portion, are formed and an optical connector 26 (see FIG. 2) is disposed at end portions of optical fibers 25 (see FIG. 2).

Here, the connector 42 is connected to the front face portion of the video processor 3 as described above, and the optical connector 26 in the connector 42 is connected to an optical connector 31 (see FIG. 2) in the video processor 3.

Configurations of the optical connector 26, the optical connector 31, the optical fibers 25, etc., will be described in detail later.

Furthermore, one end of a connection cable 43 is connected to an electric contact portion provided at a side face of the connector 42.

Inside the connection cable 43, signal wires configured to transmit a signal for driving an image pickup device 22 (see FIG. 2) in the endoscope 2 and a signal for controlling an applied voltage to be applied to an optical transmission module 24 (see FIG. 2), for example, are provided, and a connector portion at the other end of the connection cable 43 is connected to the video processor 3. The respective signals, etc., will be described in detail later.

In the distal end portion 7 of the insertion portion 6, an objective optical system (not illustrated) including a lens that allows entrance of light of an object image and an image pickup block 21 (see FIG. 2) including the image pickup device 22 arranged at an imate-forming plane of the objective optical system are disposed.

Electric configurations of the endoscope 2 and the video processor 3 in the endoscope system 1 according to the first embodiment will be described with reference to FIGS. 2 and 3.

Figure 3:
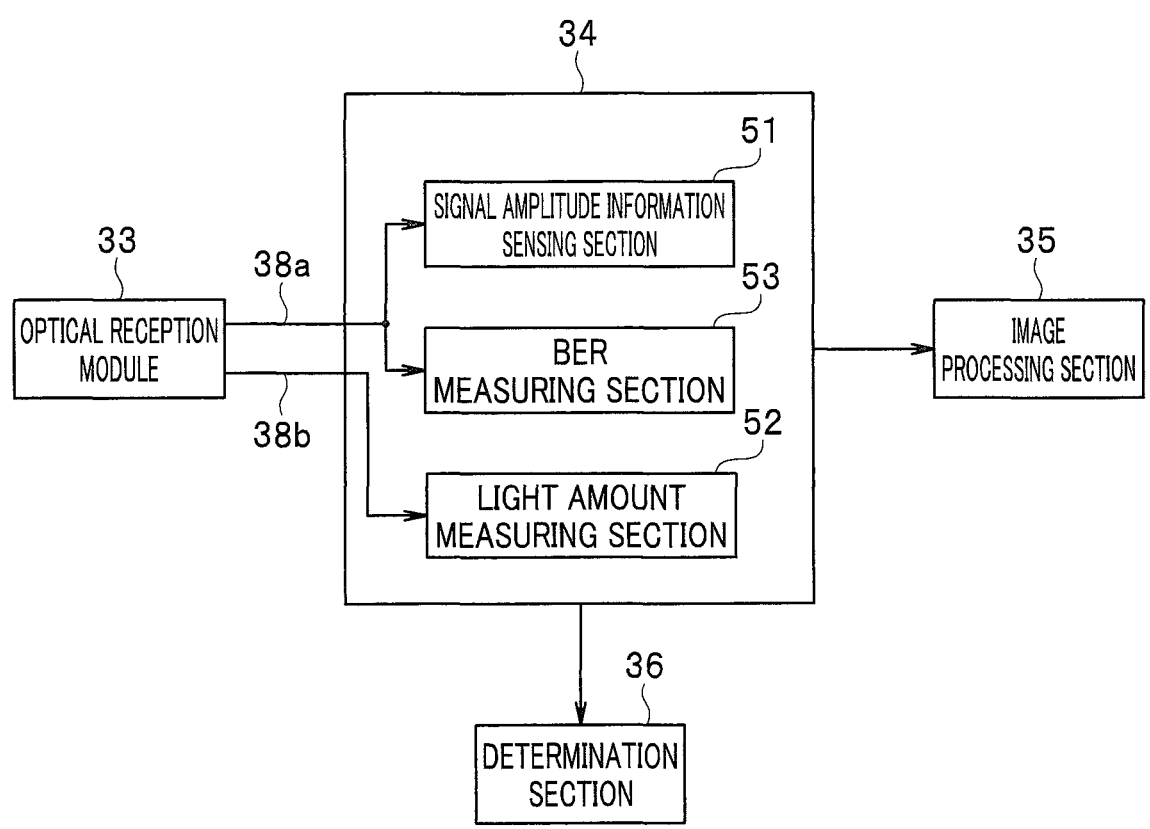
FIG. 3 is a block diagram illustrating a configuration of an information acquiring section in the endoscope system according to the first embodiment.

FIG. 2 is a block diagram illustrating an electric configuration of the endoscope system according to the first embodiment and FIG. 3 is a block diagram illustrating a configuration of an information acquiring section in the endoscope system according to the first embodiment.

<Configuration of Endoscope 2>

First, the endoscope 2 will be described.

As illustrated in FIG. 2, from the electrical perspective, the endoscope 2 includes the image pickup block 21 disposed in the distal end portion 7 of the insertion portion 6, an optical transmission module 24 disposed on the rear end side of the image pickup block 21, the optical fibers 25 provided so as to extend from the optical transmission module 24, the optical connector 26 disposed at the end portions of the optical fibers 25, and an input voltage supply line 27 for transferring an input voltage (applied voltage) to be applied to the optical transmission module 24.

Also, the endoscope 2 includes the connector 42 connected to the video processor 3, and in the connector 42, e.g., a connector circuit (not illustrated) in which an ID memory (not illustrated) that stores ID information unique to the endoscope 2 and various other circuits are formed, and the optical connector 26 are disposed, and the fluid conduit connection pipe sleeve (not illustrated) and the light guide pipe sleeve (not illustrated) are also disposed.

Furthermore, the endoscope 2 includes a cable 28 connecting the connector circuit (not illustrated) and the image pickup block 21. Inside the cable 28, a signal wire for transmitting a control signal for driving the image pickup device 22 (for example, a control signal indicating initial setting completion, which will be described later), the control signal being inputted from the video processor 3, and a power supply wire (input voltage supply line 27) for transmitting an applied voltage to be applied to the optical transmission module 24 (see FIG. 2) are provided, for example.

In the present embodiment, the image pickup block 21 includes the image pickup device 22 arranged at the image-forming plane of the objective optical system, and the signal amplitude measuring section 23 configured to measure a signal amplitude of a predetermined test signal outputted from the image pickup device 22 at the time of initial setting immediately after the endoscope 2 is powered on.

For the image pickup device 22, in the present embodiment, an image pickup device configured by a CMOS (complementary metal-oxide semiconductor) image sensor is employed.

Although not illustrated in FIG. 2, in the present embodiment, the image pickup device 22 includes a photodiode, which is a photoelectric conversion section, and also includes a timing generator and what is called an AFE (analog front-end) including an A/D conversion section, for example.

Furthermore, the image pickup device 22 is configured to output a predetermined test signal as a first electric signal, in addition to an image pickup signal resulting from pickup of an image of a subject. The test signal is a predetermined test signal outputted from the image pickup device 22 at the time of initial setting immediately after a start of activation of the image pickup device 22 when the endoscope 2 is powered on during a period until the image pickup signal of the subject is outputted (during period until the initial setting is completed).

In the present embodiment, for the test signal, what is called a PRBS (pseudo-random bit sequence) is employed.

The image pickup device 22 is configured to be controlled by a control signal from a determination section 36 (which will be described later) in the video processor 3, that is, upon recognizing completion of initial setting by receipt of a control signal indicating "initial setting completion", make a switch from the test signal to an image pickup signal and output the image pickup signal.

On the other hand, the signal amplitude measuring section 23, which is a signal amplitude measuring circuit, is configured to measure a signal amplitude of the test signal outputted from the image pickup device 22 and add signal amplitude information, which is a result of the measurement, to the test signal.

In the present embodiment, the signal amplitude measuring section 23 is configured separately from the image pickup device 22 inside the image pickup block 21; however, the present invention is independently of this configuration and may be configured to be incorporated in the image pickup device 22.

The optical transmission module 24 includes a light emitting element to be driven by a predetermined applied voltage, the light emitting element being configured to convert the image pickup signal or the test signal outputted from the image pickup device 22 (as described above, these signals are each referred to as a "first electric signal") into an optical signal and output the optical signal.

<Configuration of Optical Transmission Module 24>

Here, a configuration of the optical transmission module 24 will be described with reference to FIGS. 6 to 9.

Figure 6:
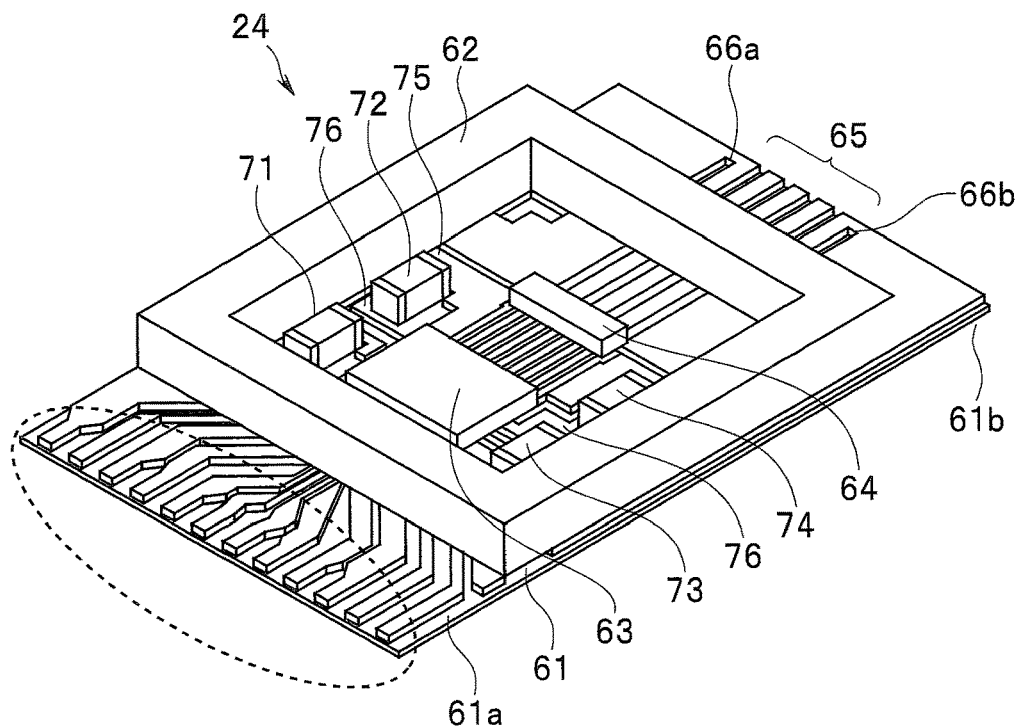
FIG. 6 is a major part perspective view illustrating an internal configuration of an optical transmission module in the endoscope system according to the first embodiment.

The optical transmission module 24 is disposed in the vicinity of the image pickup block 21 in the distal end portion 7 of the insertion portion 6. More specifically, as illustrated in FIG. 6, an internal configuration of the optical transmission module 24 includes an FPC board 61 on which various members are placed, and a resin frame 62 is disposed on an upper face of the FPC board 61. Furthermore, inside the resin frame 62, a VCSEL 64, a VCSEL driver 63 and four capacitors 71, 72, 73, 74 are disposed.

The VCSEL (vertical-cavity surface-emitting laser) 64 is a semiconductor laser configured to resonate light in a direction perpendicular to a board surface and emit the light in the direction perpendicular to the surface.

In the present embodiment, the VCSEL 64 is a light emitting element to be driven by the VCSEL driver 63, the light emitting element being configured to convert the input image pickup signal or the input test signal into an optical signal and output the optical signal to the optical fibers 25.

Figure 7:
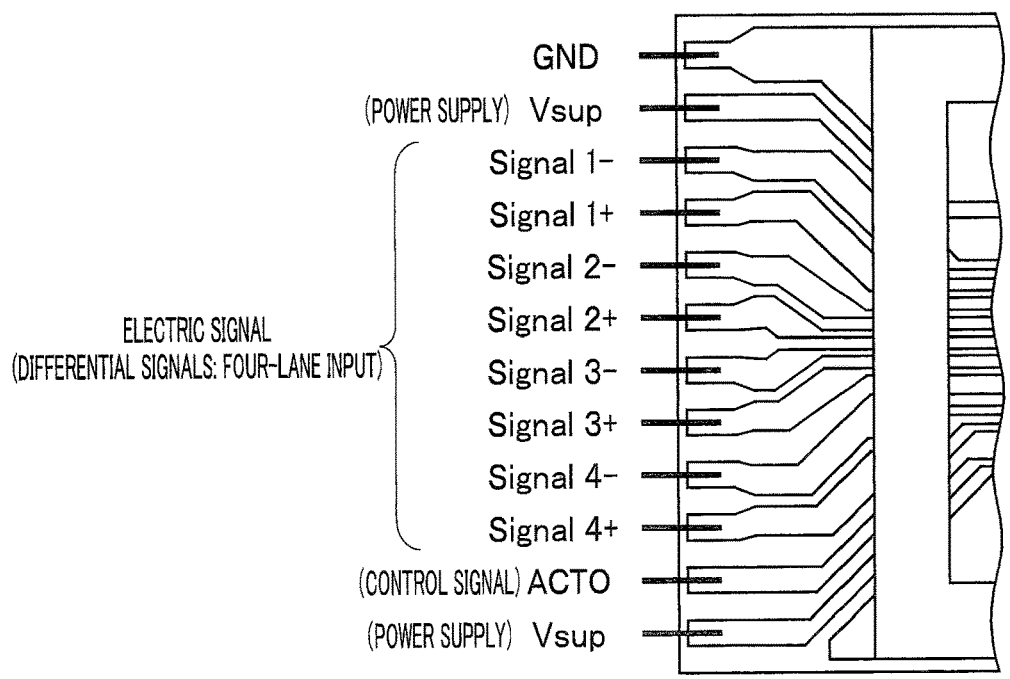
FIG. 7 is a major part enlarged view illustrating one end portion of a board of the optical transmission module in the endoscope system according to the first embodiment.

Also, as illustrated in FIG. 7, an electrode-side end portion 61a of the FPC board 61 includes power supply lines, a control signal line and four-lane input terminals that receive differential signals. Furthermore, in an optical fiber-side end portion 61b of the FPC board 61, four optical fiber groove portions 65 for installing four optical fibers 25 are formed.

Here, as illustrated in FIG. 6, respective end portions of the optical fibers 25 are installed in the respective optical fiber groove portions 65, and furthermore, when respective distal end portions of the optical fibers 25 are connected to the VCSEL 64 inside the resin frame 62, the optical fibers 25 are bonded and fixed to a lower face of the resin frame 62.

At this time, if no countermeasures are taken for an adhesive used for bonding of the optical fibers 25, a part of the adhesive may flow peripherally, for example, to the FPC board 61.

If such situation occurs, the FPC board 61 may be deformed by thermal expansion of the adhesive depending on, for example, atmospheric temperature and humidity, and consequently, detachment or displacement of the VCSEL 64 may occur.

Figure 8:
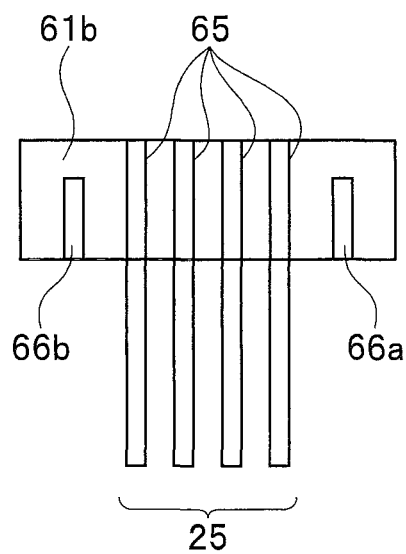
FIG. 8 is a major part enlarged view illustrating the other end portion of the board of the optical transmission module in the endoscope system according to the first embodiment.

In view of the aforementioned circumstances, as illustrated in FIG. 8, in the optical transmission module 24 employed in the present embodiment, groove portions 66a, 66b are formed in the vicinity of the optical fiber groove portions 65, more specifically, opposite end portions of the optical fiber groove portions 65, respectively, in the FPC board 61.

As a result of the groove portions 66a, 66b being formed at the optical fiber-side end portion 61b of the FPC board 61 as described above, even if a part of the adhesive for bonding of the optical fibers 25 flows out, the flowing adhesive can be caught in the groove portions 66a, 66b.

In the optical transmission module 24 in the present embodiment, the above-described configuration prevents the flown-out adhesive from flowing out to a further peripheral portion and exerts an effect of enabling prevention of deformation of the FPC board 61 due to atmospheric temperature and humidity.

On the other hand, in the present embodiment, as described above, the optical transmission module 24 includes four capacitors 71, 72, 73, 74 disposed on the upper face of the FPC board 61 inside the resin frame 62.

Here, the capacitors 71, 72, 73, 74 of this type are generally mounted on an upper face of a copper foil 75 formed on an upper face of a base material 76 of the FPC board 61. However, in recent years, for endoscopes for which size and diameter further reduction is desired, even a reduction by an amount corresponding to a thickness of the copper foil 75 is desirable.

Figure 9:
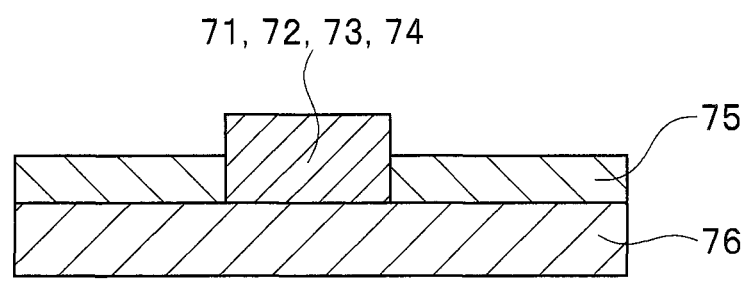
FIG. 9 is a major part enlarged cross-sectional view illustrating an arrangement of capacitors inside the optical transmission module in the endoscope system according to the first embodiment.

In view of the aforementioned circumstances, as illustrated in FIG. 9, in the optical transmission module 24 employed in the present embodiment, copper foil parts corresponding to parts in which the capacitors 71, 72, 73, 74 are mounted are shaven off, and the capacitors 71, 72, 73, 74 are directly mounted on an upper face of the base material 76.

In the optical transmission module 24 in the present embodiment, the above-described configuration exerts an effect of enabling further reduction in diameter of the distal end portion of the insertion portion 6 of the endoscope 2.

Referring back to FIG. 2, the endoscope 2 includes the optical fibers 25 provided so as to extend from the optical transmission module 24. Each of the optical fibers 25 is a multimode fiber having a core diameter of 50 μm and is provided so as to extend from the optical transmission module 24 (more specifically, as described above, the VCSEL 64 inside the optical transmission module 24) disposed in the distal end portion 7 of the insertion portion 6 to the optical connector 26 disposed in the connector 42 through the respective insides of the insertion portion 6, the operation section 10 and the universal cord 41.

As described above, in the present embodiment, the optical fibers 25 are four fibers to correspond to the four-lane differential signal lines.

Also, as described above, the optical connector 26 is disposed at the distal end portions of the optical fibers 25. The optical connector 26 forms a part of the connector 42 and is optically connected to the optical connector 31 in the video processor 3.

On the other hand, as illustrated in FIG. 2, the endoscope 2 includes the input voltage supply line 27 for transferring an input voltage (applied voltage) to be applied to the optical transmission module 24. The input voltage supply line 27 is connected to a power supply adjusting section 37 (details will be described later) in the video processor 3 and is configured to apply a voltage adjusted by the power supply adjusting section 37 to the optical transmission module 24.

Here, as described above, in general, this type of optical transmission module is set to be driven at an optimum input voltage (applied voltage). However, the input voltage (applied voltage) cannot be changed from an initial setting by design.

Then, for example, if a failure in connection between the optical connector 26 and the optical connector 31 (due to, e.g., dirt or displacement) in an optical signal transmission path, or, for example, if, e.g., a breakage occurs in the portion of connection with the optical fibers 25 in the optical transmission module 24, as described above, light amount reduction or jitter worsening may occur.

In the case of occurrence of such trouble, if the input voltage (applied voltage) for the optical transmission module 24 cannot be changed as described above, it is difficult to provide an optical transmission system with good transmission quality.

In view of the aforementioned circumstances, the present embodiment is intended to enable control of an input voltage (applied voltage) for the optical transmission module 24 so that optimum transmission quality is consistently provided for an optical signal.

More specifically, the input voltage (applied voltage) for the optical transmission module 24 in the endoscope 2 is outputted after adjustment and control of the input voltage by the determination section 36 and the power supply adjusting section 37 on the video processor 3 side, and applied to the optical transmission module 24 through the input voltage supply line 27. The control from the video processor 3 side will be described in detail later.

<Configuration of Video Processor 3>

Next, a configuration of the video processor 3 will be described.

The video processor 3 is a signal processing apparatus connected to the endoscope 2, the signal processing apparatus being configured to also function as a light source apparatus, and receive an input of the image pickup signal and subject the image pickup signal to predetermined image processing, and in the present embodiment, as described above, the video processor 3 also functions as an information processing apparatus that receives an input of the test signal outputted from the endoscope 2 prior to the image pickup signal when the endoscope 2 is powered on (at the time of power-on) and performs predetermined information processing.

More specifically, as illustrated in FIG. 2, the video processor 3 includes the optical connector 31 optically connected to the optical connector 26, optical fibers 32 provided so as to extend from the optical connector 31 and an optical reception module 33 connected to an end of the optical fibers 32.

The video processor 3 further includes an information acquiring section 34 connected to a first output wire 38a and a second output wire 38b, which are output ends of the optical reception module 33, an image processing section 35 connected to an output end of the information acquiring section 34, the image processing section 35 being configured to perform predetermined image processing on an image pickup signal from the image pickup device 22, the determination section 36 configured to perform predetermined determination based on various types of information acquired by the information acquiring section 34, and a power supply adjusting section 37 configured to adjust an input voltage (applied voltage) for the optical transmission module 24 in the endoscope 2 based on a result of the determination by the determination section 36 and output the input voltage (applied voltage).

The optical fibers 32 in the video processor 3 have a configuration that is similar to the configuration of the optical fibers 25 and are configured to transmit the image pickup signal or the test signal that is an optical signal.

The optical reception module 33 includes a light receiving element configured to receive the image pickup signal or the test signal that is an optical signal, which is transmitted by the optical fibers 32, and convert the image pickup signal or the test signal into a predetermined electric signal and output the electric signal.

Here, the optical reception module 33 is configured to convert the optical signal (the image pickup signal or the test signal) which enters the light receiving element into a predetermined electric signal and output the converted electric signal as a second electric signal from the first output wire 38a (see FIGS. 2 and 3).

Also, the optical reception module 33 is configured to output an electric signal indicating current value information corresponding to a light amount of the optical signal which enters the light receiving element from the second output wire 38b as a third electric signal (see FIGS. 2 and 3).

<Configuration of Information Acquiring Section 34>

Next, a configuration of the information acquiring section 34 will be described with reference to FIG. 3.

As illustrated in FIG. 3, the information acquiring section 34, which is an information acquiring circuit, includes a signal amplitude information sensing section 51 and a BER measuring section 53 connected to the output wire 38a from the optical reception module 33, and a light amount measuring section 52 connected to the output wire 38b from the optical reception module 33.

The signal amplitude information sensing section 51 as a signal amplitude information sensing circuit has a function that senses the signal amplitude information based on the test signal converted into an electric signal by the optical reception module 33.

In other words, the signal amplitude information sensing section 51 is connected to the first output wire 38a from the optical reception module 33 and is configured to receive an input of the second electric signal outputted from the optical reception module 33 (predetermined electric signal obtained as a result of the conversion of the optical signal which enters the optical reception module 33).

Here, as described above, the signal amplitude measuring section 23 in the endoscope 2 adds signal amplitude information, which is a result of measurement by the signal amplitude measuring section 23, to a test signal outputted from the image pickup block 21 (as described above, in the present embodiment, as well as the image pickup signal, the test signal is a first electric signal).

Then, the test signal, which is a first electric signal, is once converted into an optical signal by the optical transmission module 24 in the endoscope 2 and then converted again into an electric signal by the optical reception module 33 in the video processor 3 via the optical fibers 25 and the optical fibers 32, and outputted as a second electric signal from the first output wire 38a.

The signal amplitude information sensing section 51 senses the signal amplitude information added to the test signal based on the test signal, which is the inputted second electric signal, that is, senses an amplitude value of the test signal, and outputs a result of the sensing to the determination section 36.

Therefore, the information acquiring section 34 including the signal amplitude information sensing section 51 functions as an information acquiring section configured to acquire transmission information relating to the optical signal based on an electric signal relating to the test signal from among the electric signals outputted from the optical reception module 33.

Also, the light amount measuring section 52 as a light amount measuring circuit has a function that measures a light amount of the optical signal based on the third electric signal.

In other words, the light amount measuring section 52 is connected to the second output wire 38b from the optical reception module 33 and receives an input of the third electric signal outputted from the optical reception module 33. As described above, the third electric signal is an electric signal indicating current value information corresponding to a light amount of an optical signal which enters the optical reception module 33.

Then, the light amount measuring section 52 measures a value of the light amount of the optical signal which enters the optical reception module 33 based on the third electric signal indicating current value information corresponding to the light amount of the optical signal and outputs a result of the measurement to the determination section 36.

Furthermore, the BER measuring section 53, which is a bit error rate measuring circuit, has a function as a bit error rate measuring section configured to measure a bit error rate (BER) of the optical signal based on the test signal that is the second electric signal.

In other words, the BER measuring section 53 is connected to the first output wire 38a from the optical reception module 33 and receives an input of the second electric signal outputted from the optical reception module 33 (predetermined electric signal obtained as a result of conversion of the optical signal which enters the optical reception module 33).

Then, the BER measuring section 53 measures a bit error rate (BER) of the test signal based on the test signal that is the inputted second electric signal and outputs a result of the measurement to the determination section 36.

Furthermore, the BER measuring section 53 determines whether the inputted second electric signal is the test signal or an image pickup signal, and if a result of the determination is that the second electric signal is an image pickup signal, outputs the image pickup signal to the image processing section 35.

<Determination in Determination Section 36>

Referring back to FIG. 2, the determination section 36, which is a determination apparatus, obtains the results from the signal amplitude information sensing section 51, the light amount measuring section 52 and the BER measuring section 53 in the information acquiring section 34 and determines a transmission state (transmission quality) of the test signal.

In other words, the determination section 36 is configured to obtain the above respective pieces of information relating to the transmission quality of the test signal (the result of the "amplitude" sensing by the signal amplitude information sensing section 51, the result of the "light amount" measurement by the light amount measuring section 52 or the result of "BER" measurement by the BER measuring section 53) from the information acquiring section 34, and based on the respective obtained results, determine whether the transmission quality is good or poor according to determination criteria (criterion values for satisfactory transmission quality) determined in advance for the respective pieces of information.

Also, the determination section 36 is configured to determine a pattern of a combination of "good" and/or "poor" in transmission quality for the pieces of information according to determination of whether the transmission quality is good or poor for each of the pieces of information.

Furthermore, according to the determined pattern, the determination section 36 performs any of respective types of processing including, e.g.,
(a) controlling the power supply adjusting section 37 to cause the power supply adjusting section 37 to adjust an input voltage (applied voltage) for the optical transmission module 24 in the endoscope 2 and output the input voltage to the optical transmission module 24;
(b) transmitting a control signal indicating "initial setting completion" to the image pickup block 21 to switch a test signal outputted from the image pickup block 21 to an image pickup signal; and
(c) regarding an error as occurring, controlling the respective related circuits to provide predetermined error display on the monitor 5.

Furthermore, the determination section 36 is configured to also determine whether or not the input voltage (applied voltage) adjusted by the power supply adjusting section 37 has a value within a specified value range for the optical transmission module 24.

More specifically, when the determination section 36 performs processing (a) above, the determination section 36 also determines whether or not a voltage to be applied to the optical transmission module 24 has a value within the specified value range for the optical transmission module 24 and if the determination section 36 determines that the voltage has a value outside the specified value range, the determination section 36 regards an error as occurring and controls the respective related circuits to provide predetermined error display on the monitor 5.

Here, if the determination section 36 determines that a voltage to be applied to the optical transmission module 24 has a value within the specified value range for the optical transmission module 24, the determination section 36 performs processing (a) above. That is, the determination section 36 has a function as a voltage monitoring apparatus configured to monitor whether or not a value of the applied voltage is within a predetermined specified value range.

<Adjustment of Input Voltage (Applied Voltage) for the Optical Transmission Module 24, by the Power Supply Adjusting Section 37>

According to the results of determination by the determination section 36, if predetermined conditions are met, the power supply adjusting section 37, which is a power supply adjusting circuit, adjusts the input voltage (applied voltage) for the optical transmission module 24 and outputs the resulting input voltage to the input voltage supply line 27 in the endoscope 2.

<Operation of First Embodiment>

Operation of the first embodiment configured as described above will be described with reference to FIGS. 4 and 5.

Figure 4:
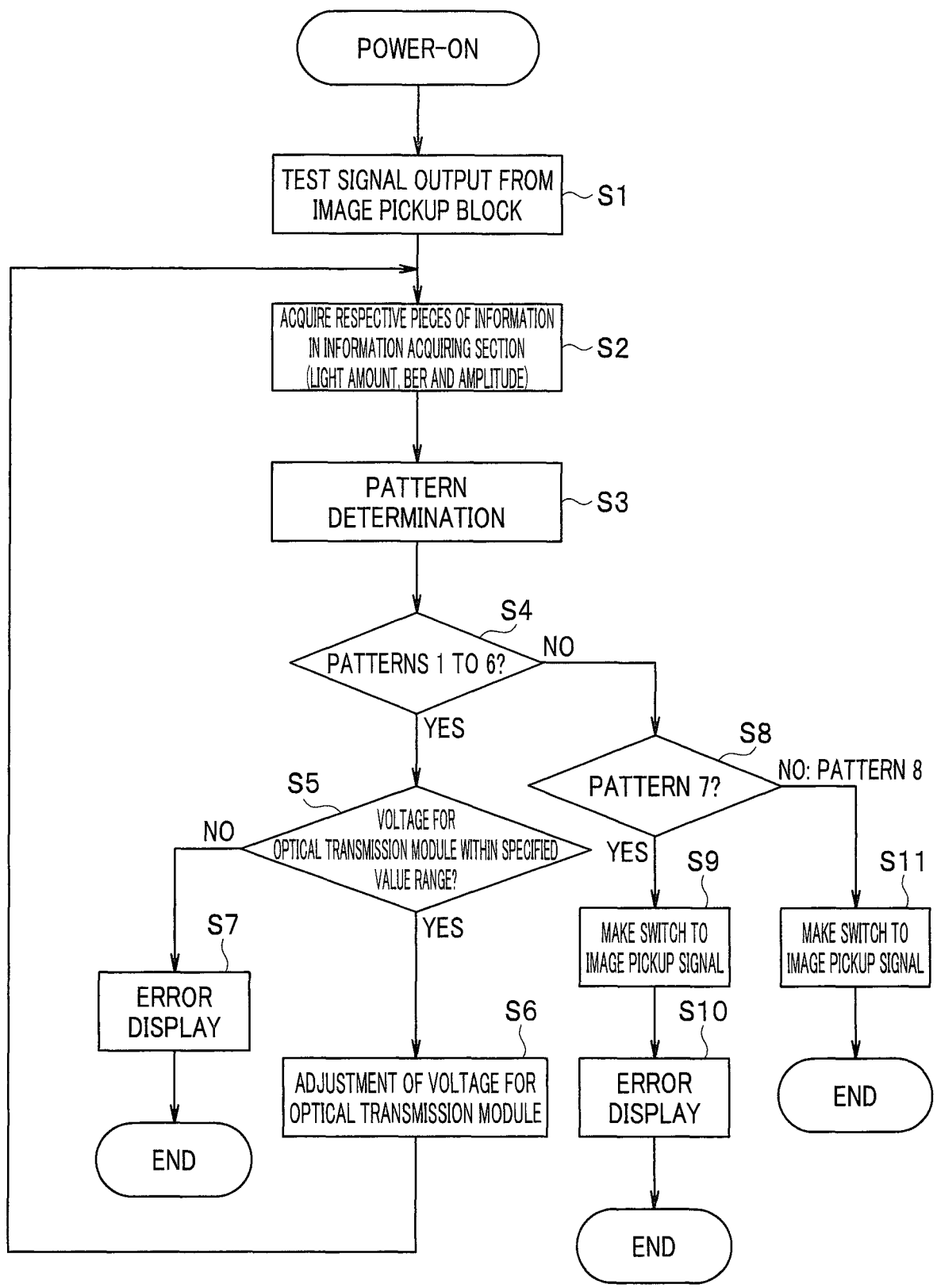
FIG. 4 is a flowchart of a transmission quality control operation in the endoscope system according to the first embodiment.

FIG. 4 is a flowchart illustrating a transmission quality control operation in the endoscope system according to the first embodiment, and FIG. 5 is a table indicating processing performed by a determination section for each of patterns related to respective pieces of information acquired by an information acquiring section in the endoscope system according to the first embodiment.

As illustrated in FIG. 4, upon the endoscope system 1 (the endoscope 2 and the video processor 3) being powered on, the test signal from the image pickup block 21 (image pickup device 22) is outputted as a first electric signal (step S1). At this time, as described above, the test signal is added with signal amplitude information measured by the signal amplitude measuring section 23.

In step S1, the test signal outputted from the image pickup block 21 is converted into an optical signal by the optical transmission module 24, and then transmitted through the optical fibers 25, the optical connector 26, the optical connector 31 and the optical fibers 32 and then inputted to the optical reception module 33.

Then, the test signal converted again into an electric signal (second electric signal) by the optical reception module 33 is inputted to respective sections (the signal amplitude information sensing section 51 and the BER measuring section 53) in the information acquiring section 34 via the first output wire 38a.

On the other hand, a third electric signal indicating current value information corresponding to a light amount of the optical signal is outputted from the optical reception module 33, and the third electric signal is inputted to the light amount measuring section 52 in the information acquiring section 34 via the second output wire 38b.

Next, the respective sections (the signal amplitude information sensing section 51, the light amount measuring section 52 and the BER measuring section 53) in the information acquiring section 34 acquire the amplitude information, the light amount information and the BER information, respectively, based on the test signal that is the second electric signal or the third electric signal relating to a value of the light amount (step S2), and output the respective acquired pieces of information to the determination section 36.

Subsequently, the determination section 36 first determines a pattern related to the pieces of information acquired by the information acquiring section 34, based on the pieces of information (the amplitude information, the light amount information and the BER information) (step S3).

In other words, as described above, the determination section 36 obtains the above respective pieces of information relating to transmission quality of the test signal (the result of "amplitude" sensing by the signal amplitude information sensing section 51, the result of "light amount" measurement by the light amount measuring section 52 or the result of "BER" measurement by the BER measuring section 53) from the information acquiring section 34 and based on the obtained results, determines whether the transmission quality is good or poor according to determination criterions (criterion values for satisfactory transmission quality) determined in advance for the respective pieces of information.

Then, the determination section 36 determines a pattern corresponding to a combination of "good" and/or "poor" according to determination of whether the transmission quality is good or power for each of the pieces of information (step S3).

Subsequently, the determination section 36 controls the related circuits to perform the relevant processing according to the determined pattern (steps S4 to S7 or steps S8 to S11).

Here, the respective patterns and the contents of the respective types of processing for the patterns will be described with reference to FIG. 5.

As described above, the determination section 36 is configured to based on respective results obtained from the information acquiring section 34, determine whether transmission quality is good or poor according to the determination criterions (criterion values for satisfactory transmission quality) determined in advance for the respective pieces of information.

In FIG. 5, mark "O" in the table indicates a state in which the determination criterion (criterion value for satisfactory transmission quality) for the relevant piece of information is met (state of "good"), and mark "X" indicates a state in which the determination criterion (criterion value for satisfactory transmission quality) for the relevant piece of information is not met (state of "poor").

Then, the respective patterns (patterns 1 to 8) in FIG. 5 correspond to respective types of combinations of "good" and/or "poor" for the determination criterions for the respective pieces of information, and for example, pattern 1 is a pattern corresponding to Pattern 1: combination of "light amount: poor", "BER: good" and "amplitude: good", and means that the "BER" and the "amplitude" are "good" and are within respective criterion value ranges but the "light amount" is "poor" and is out of a relevant criterion value range.

Also, pattern 8 is a pattern corresponding to pattern 8: combination of "light amount: good", "BER: good" and "amplitude: good", and means that all of the "light amount", the "BER" and the "amplitude" are "good" and are within the respective criterion value ranges.

For the endoscope system according to the first embodiment, the plurality of patterns indicated below, that is, pattern 1: combination of "light amount: poor", "BER: good" and "amplitude: good", pattern 2: combination of "light amount: good", "BER: poor" and "amplitude: good", pattern 3: combination of "light amount: poor", "BER: poor" and "amplitude: good", pattern 4: combination of "light amount: poor", "BER: good" and "amplitude: poor", pattern 5: combination of "light amount: poor", "BER: poor" and "amplitude: poor", pattern 6: combination of "light amount: good", "BER: poor" and "amplitude: poor", pattern 7: combination of "light amount: good", "BER: good" and "amplitude: poor", and pattern 8: combination of "light amount: good", "BER: good" and "amplitude: good"

are specified respectively.

Here, referring back to FIG. 4, in step S3, the determination section 36 determines the pattern according to the determination of whether the transmission quality is good or poor for each of the pieces of information and if the pattern determined as a result is any of patterns 1 to 6 (step S4), the determination section 36 proceeds to next step S5.

In step S5, the determination section 36 determines whether or not the input voltage (applied voltage) adjusted by the power supply adjusting section 37 has a value within the specified value range for the optical transmission module 24 (step S5).

Then, if the determination section 36 determines in step S5 that the voltage to be applied to the optical transmission module 24 has a value outside the specified value range for the optical transmission module 24, the determination section 36 regards an error as occurring and controls the respective related circuits to provide predetermined error display on the monitor 5 (step S7).

On the other hand, if the determination section 36 determines in step S5 that the voltage to be applied to the optical transmission module 24 has a value within the specified value range for the optical transmission module 24, the determination section 36 proceeds to step S6.

In other words, in step S6, under the control of the determination section 36, the power supply adjusting section 37 adjusts the input voltage (applied voltage) for the optical transmission module 24 and outputs the input voltage to the input voltage supply line 27 in the endoscope 2.

More specifically, if the pattern determined by the determination section 36 is any of patterns 1, 2 and 3, that is, any of the following patterns:

pattern 1: combination of "light amount: poor", "BER: good" and "amplitude: good", pattern 2: combination of "light amount: good", "BER: poor" and "amplitude: good", and pattern 3: combination of "light amount: poor", "BER: poor" and "amplitude: good", the power supply adjusting section 37 adjusts the input voltage to be applied to the optical transmission module 24 to be raised by unit of, for example, no more than 0.1 [V] and outputs the resulting input voltage to the input voltage supply line 27 in the endoscope 2, and the operation returns to step S2 above.

Subsequently, steps S2 to S6 above are repeated until the pattern becomes pattern 7 or pattern 8 as a result of the adjustment (control to raise the input voltage) by the power supply adjusting section 37.

Here, it is assumed that the input voltage is adjusted to be gradually raised by the adjustment by the power supply adjusting section 37 and reaches an upper limit value of the specified value range specified for the optical transmission module 24. If the pattern yet becomes neither pattern 7 nor pattern 8 even in this case, it is determined in step S5 above that the input voltage falls outside the specified value range for the optical transmission module 24.

Then, the determination section 36 proceeds to step S7 at this timing and error display is provided on the monitor 5 under the control of the determination section 36.

On the other hand, if the pattern determined by the determination section 36 in step S6 is any of patterns 4, 5 and 6 above, that is, any of the following:

pattern 4: combination of "light amount: poor", "BER: good" and "amplitude: poor", pattern 5: combination of "light amount: poor", "BER: poor" and "amplitude: poor", and pattern 6: combination of "light amount: good", "BER: poor" and "amplitude: poor", the power supply adjusting section 37 adjusts the input voltage to be applied to the optical transmission module 24 to be lowered by unit of, for example, no more than 0.1 [V] and outputs the resulting input voltage to the input voltage supply line 27 in the endoscope 2, and the operation returns to step S2 above.

Here, a reason that the value of the input voltage to be applied to the optical transmission module 24 is increased/decreased according to whether the "amplitude is good or poor" under the control of the video processor 3 will be described.

In general, as an input voltage applied to an optical transmission module is higher, an amount of light output tends to be higher. Here, where the applied input voltage is high, if an amplitude of an input signal from the image pickup device 22 falls below the relevant specified value range, the optical transmission module may fail to operate.

However, it is known that even where the optical transmission module 24 enters such inoperable state, the optical transmission module 24 is likely to operate if the input voltage applied to the optical transmission module 24 is lowered. This seems to be because a threshold value for an amplitude of an input signal is varied by an input voltage since an IC (for example, the VCSEL driver 63) inside the optical transmission module is driven by sensing the applied input voltage and a level of an amplitude of an input signal and the input voltage and a threshold value for the amplitude of the input signal transition both substantially linearly.

The endoscope system 1 according to the present embodiment is focused on such effect above and is intended to provide an endoscope system employing an optical signal transmission method, the endoscope system being capable of preventing transmission failure and consistently providing optimum transmission quality.

On the other hand, as stated above, subsequently steps S2 to S6 above are repeated until the pattern becomes pattern 7 or pattern 8 as a result of adjustment (input voltage lowering control) by the power supply adjusting section 37.

Furthermore, as in the above, it is assumed that the input voltage is gradually lowered by adjustment of the power supply adjusting section 37 and the input voltage reaches a lower limit value of the specified value range specified for the optical transmission module 24. If the pattern yet becomes neither pattern 7 nor pattern 8 even in such case, it is determined in step S5 above that the input voltage falls outside the specified value range for the optical transmission module 24. Then, in this case, also, the determination section 36 proceeds to step S7 and under the control of the determination section 36, error display is provided on the monitor 5.

Also, in step S4 above, if the determined pattern is pattern 7 or pattern 8, the determination section 36 proceeds to step S8. Then, in step S8, the determination section 36 determines that the pattern is either pattern 7 or pattern 8 (step S8).

Here, if the pattern is pattern 7, that is, pattern 7: combination of "light amount: good", "BER: good" and "amplitude: poor", the "light amount" and the "BER" are both "good" but the "amplitude" is "poor", and thus, it can be presumed that no problem occurs in the optical signal transmission path but some problem occurs in the image pickup device 22 itself.

Therefore, if the determination section 36 determines in step S8 that the pattern is pattern 7, the determination section 36 transmits a control signal indicating "initial setting completion" to the image pickup block 21 in order to switch the test signal outputted from the image pickup block 21 to an image pickup signal (step S9).

Also, concurrently, the determination section 36 regards a failure as occurring in the image pickup device 22 and controls the respective related circuits so as to provide predetermined error display on the monitor 5 (step S10).

On the other hand, if it is determined in step S8 that the pattern is pattern 8, that is, pattern 8: combination of "light amount: good", "BER: good" and "amplitude: good", since it can be presumed that no problem occurs in either the optical signal transmission path or the image pickup device 22, the determination section 36 transmits a control signal indicating "initial setting completion" to the image pickup block 21 in order to switch the test signal outputted from the image pickup block 21 to an image pickup signal (step S11).

As described above, the present embodiment enables an endoscope system employing an optical signal transmission method, to accurately detect a transmission state (transmission quality) of an optical signal in the video processor 3 based on a first electric signal (test signal) outputted from the image pickup device 22 at the time of initial setting immediately after a start of activation of the image pickup device 22 upon the endoscope 2 being powered on and to based on a result of the detection, adjust and control an input voltage to be applied to the endoscope 2-side optical transmission module 24, enabling achievement of optical transmission that is consistently good in transmission quality even if transmission quality (for example, a light amount and/or jitter) deteriorates in the optical signal transmission path and also enabling prevention of transmission failure even if an amplitude of the relevant image pickup signal becomes small because of, e.g., operation failure in the image pickup device 22.

Also, as described above, the first embodiment is configured so that the video processor 3 accurately detects a transmission state (transmission quality) of an optical signal based on a test signal that is a first electric signal outputted from the image pickup device 22, but detection of a transmission state of an optical signal in the present invention is independently of detection based on a test signal such as described above and may be detection based on an image pickup signal outputted from the image pickup device 22.

In this case, not only at the time of initial setting immediately after a start of activation of the image pickup device 22 when the endoscope 2 is powered on, but also at the time of normal shooting, operation and effects similar to the above can be provided, that is, optical transmission that is consistently good in transmission quality in the optical signal transmission path even if transmission quality (for example, a light amount and/or jitter) deteriorates can be achieved and transmission failure can be prevented even if an amplitude of the relevant image pickup signal becomes small because of, e.g., operation failure in the image pickup device 22.

<First Modification>

Next, a first modification of the first embodiment of the present invention will be described.

Figure 10:
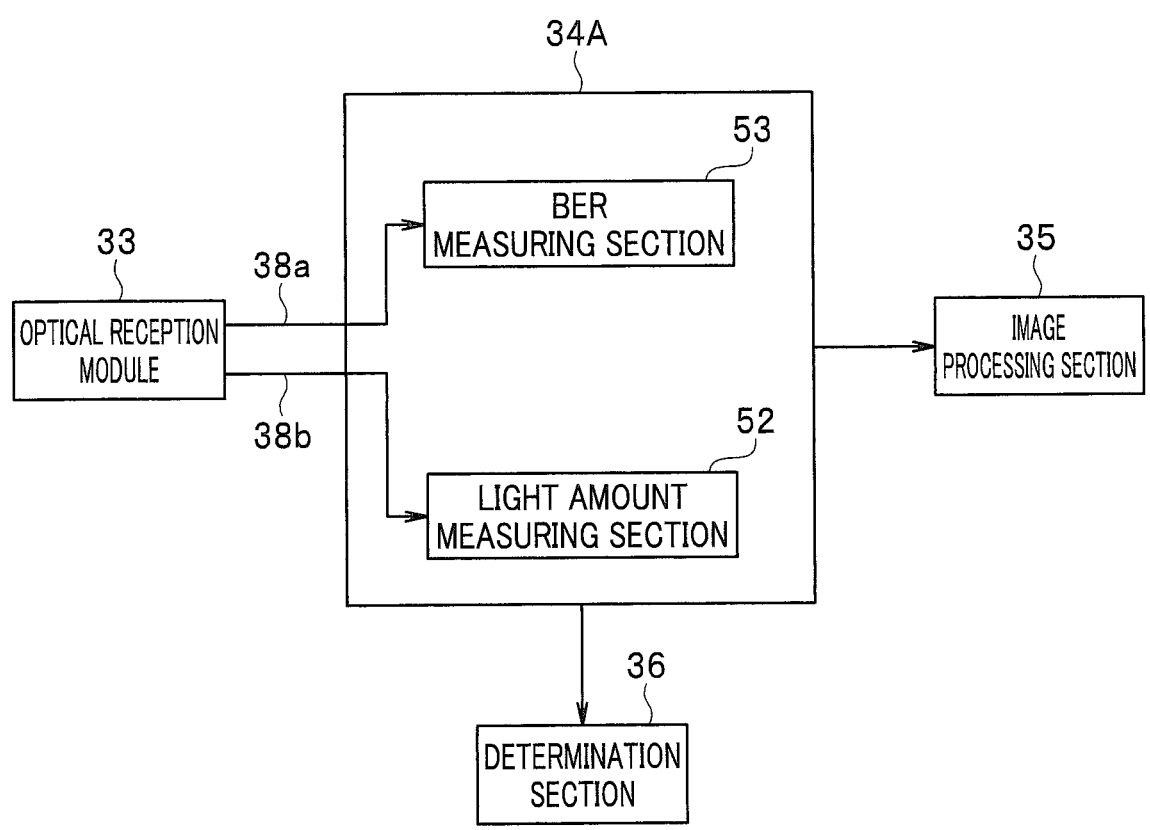
FIG. 10 is a block diagram illustrating a configuration of an information acquiring section in an endoscope system according to a first modification of the first embodiment.
Figure 11:
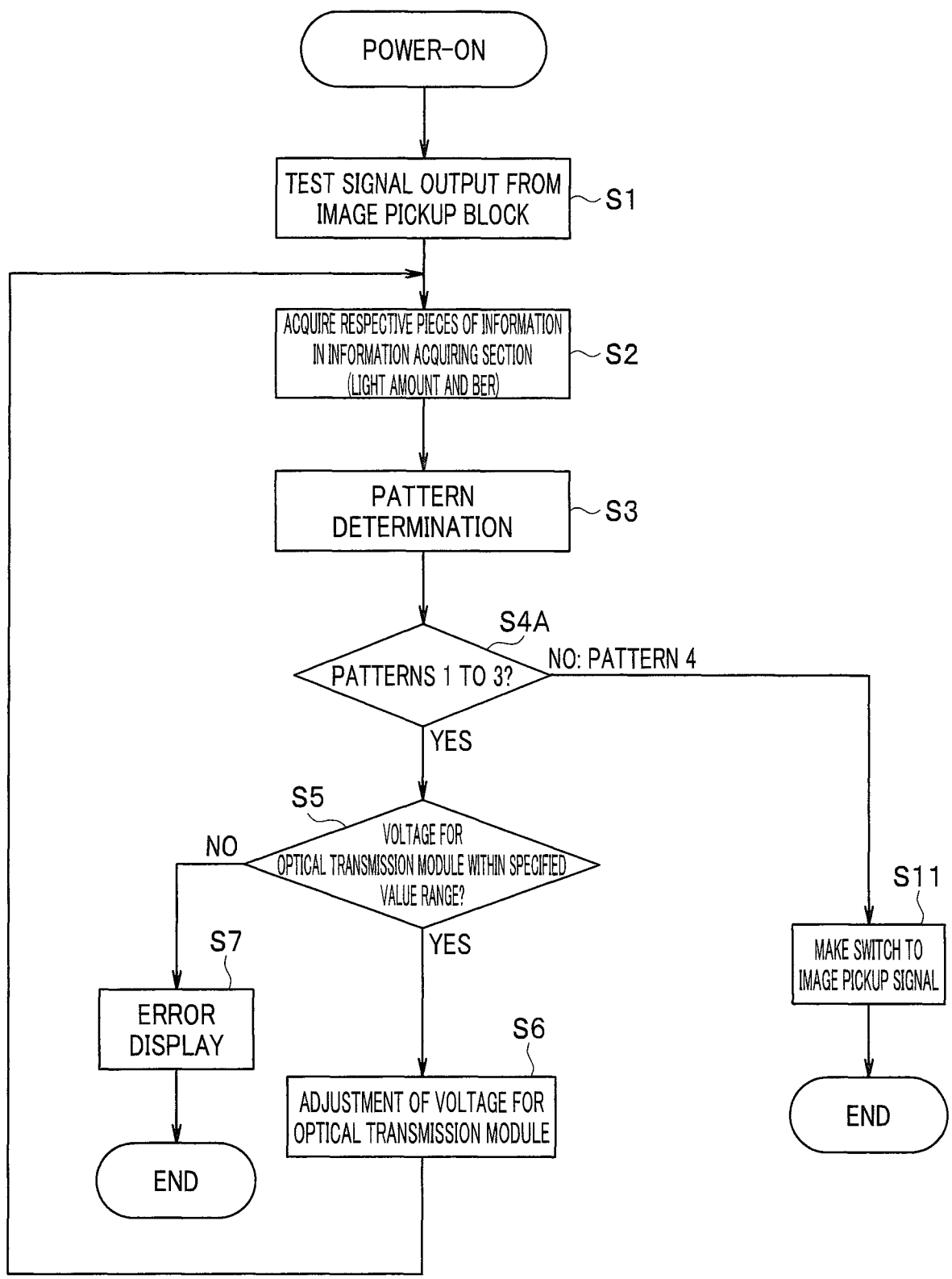
FIG. 11 is a flowchart illustrating a transmission quality control operation in the endoscope system according to the first modification of the first embodiment.
Figures 12, 13:
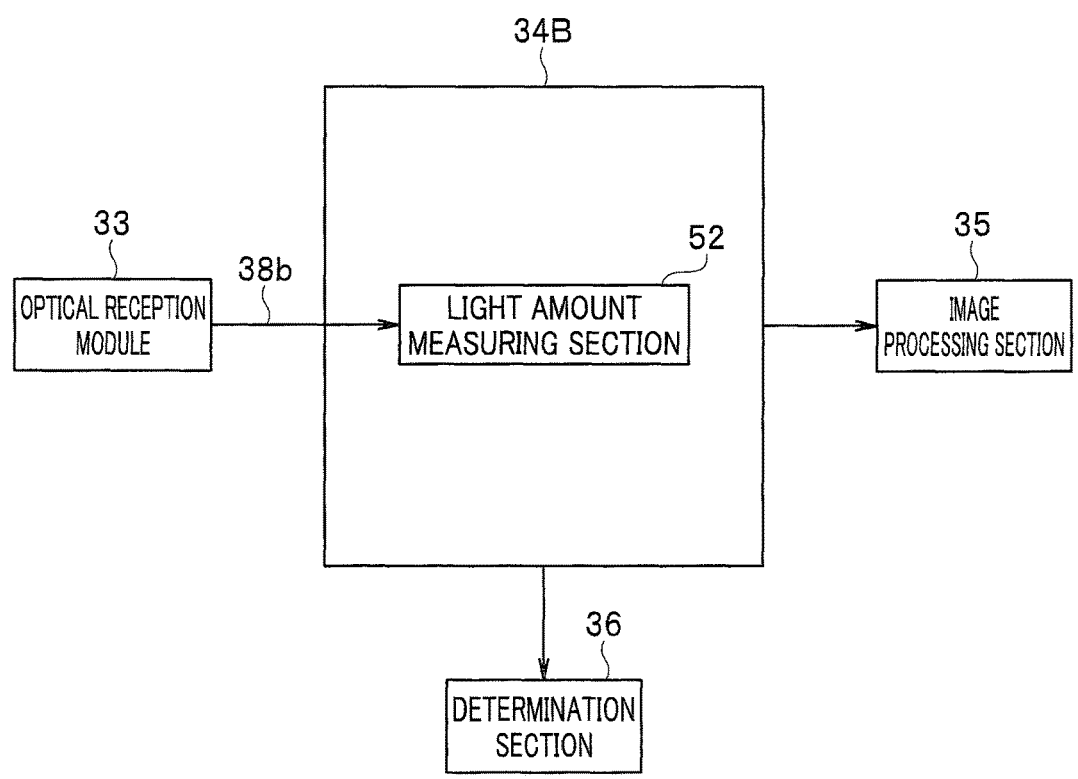
FIG. 12 is a table indicating processing performed by a determination section for each of patterns related to respective pieces of information acquired by an information acquiring section in the endoscope system according to the first modification of the first embodiment.
FIG. 13 is a block diagram illustrating a configuration of an information acquiring section in an endoscope system according to a second modification of the first embodiment.

FIG. 10 is a block diagram illustrating a configuration of an information acquiring section in an endoscope system according to a first modification of the first embodiment, FIG. 11 is a flowchart illustrating a transmission quality control operation in the endoscope system according to the first modification of the first embodiment, and FIG. 12 is a table indicating processing performed by a determination section for each of patterns related to respective pieces of information acquired by an information acquiring section in the endoscope system according to the first modification of the first embodiment.

The endoscope system according to the first modification is similar in basic configuration to the first embodiment but is only partially different in configuration of an information acquiring section 34A in a video processor 3 and in contents of measurement results used by a determination section 36 from the first embodiment. Therefore, here, only differences from the first embodiment will be described and description of parts in common with the first embodiment will be omitted.

As illustrated in FIG. 10, the information acquiring section 34A according to the first modification includes a BER measuring section 53 connected to a first output wire 38a extending from an optical reception module 33 and a light amount measuring section 52 connected to a second output wire 38b also extending from an optical reception module 33.

Also, as illustrated in FIG. 11, in the endoscope system 1 according to the first modification, as in the above, in step S1, a test signal is outputted from an image pickup block 21, and the test signal is converted into an optical signal by an optical transmission module 24 and then transmitted through optical fibers 25, an optical connector 26, an optical connector 31 and optical fibers 32 and then inputted to the optical reception module 33.

The test signal converted into a second electric signal by the optical reception module 33 is inputted to the BER measuring section 53 in the information acquiring section 34A via the first output wire 38a. On the other hand, a third electric signal outputted from the optical reception module 33, the third electric signal relating to a value of a light amount, is inputted to the light amount measuring section 52 in the information acquiring section 34A via the second output wire 38b.

Next, the respective sections (the light amount measuring section 52 and the BER measuring section 53) in the information acquiring section 34A acquire light amount information and BER information, respectively, based on the test signal that is the second electric signal or the third electric signal relating to the value of the light amount (step S2), and output the respective acquired pieces of information to a determination section 36.

Subsequently, the determination section 36 determines a pattern related to the pieces of information acquired by the information acquiring section 34A, based on the pieces of information (the light amount information and the BER information) and determines whether transmission quality is good or poor according to determination criterions (criterion values for satisfactory transmission quality) determined in advance for the respective pieces of information (step S3).

Subsequently, the determination section 36 controls related circuits to perform relevant processing according to the determined pattern (steps S4A to S7 or step S11).

Here, respective patterns and contents of respective types of processing for the patterns will be described with reference to FIG. 12. In FIG. 12, as in the first embodiment, marks "O" and "X " in the table indicates whether a determination criterion (criterion value for satisfactory transmission quality) for the relevant piece of information is met or not.

In FIG. 12, the respective patterns (patterns 1 to 4) correspond to respective types of combinations of "good" and/or "poor" for the determination criterions for the respective pieces of information, and for the endoscope system according to the first modification, the respective patterns indicated below are specified:

pattern 1: combination of "light amount: poor" and "BER: good", pattern 2: combination of "light amount: poor" and "BER: poor", pattern 3: combination of "light amount: good" and "BER: poor", and pattern 4: combination of "light amount: good" and "BER: good".

Referring back to FIG. 11, in step S3, the determination section 36 determine the pattern according to the determination of whether the transmission quality is good or poor for each of the pieces of information and if the pattern determined as a result is any of patterns 1 to 3 (step S4A), the determination section 36 proceeds to next step S5.

In steps S5 to S7 in the first modification, operation that is similar to the operation of the first embodiment is performed. More specifically, if the pattern determined by the determination section 36 is any of patterns 1, 2 and 3 above, that is, any of the following patterns:

pattern 1: combination of "light amount: poor" and "BER: good", pattern 2: combination of "light amount: poor" and "BER: poor", and pattern 3: combination of "light amount: good" and "BER: poor", the power supply adjusting section 37 adjusts an input voltage to be applied to the optical transmission module 24 to be raised by unit of, for example, no more than 0.1 [V] and outputs the resulting input voltage to an input voltage supply line 27 in an endoscope 2 and the operation returns to step S2 above.

Subsequently, steps S2 to S6 above are repeated until the pattern becomes pattern 4: "light amount: good" and "BER: good" as a result of the adjustment (control to raise the input voltage) by the power supply adjusting section 37.

Here, it is assumed that the input voltage is adjusted to be gradually raised by the adjustment by the power supply adjusting section 37 and reaches an upper limit value of a specified value range specified for the optical transmission module 24. If the pattern does not yet become pattern 4: "light amount: good" and "BER: good" even in this case, it is determined as follows. In other words, it is determined in step S5 above that the input voltage falls outside the specified value range for the optical transmission module 24.

Therefore, as in the above, the determination section 36 proceeds to step S7 at this timing and error display is provided on a monitor 5 under the control of the determination section 36.

On the other hand, if the pattern determined in step S4A above is pattern 4: "light amount: good" and "BER: good", it can be presumed that no problem occurs in both an optical signal transmission path and an image pickup device 22. Consequently, the determination section 36 transmits a control signal indicating "initial setting completion" to the image pickup block 21 (step S11).

As described above, the first modification also enables achieving optical transmission that is consistently good in transmission quality in the optical signal transmission path even if transmission quality (for example, a light amount and/or jitter) deteriorates, and enables preventing transmission failure even if an amplitude of the relevant image pickup signal becomes small because of, e.g., operation failure in the image pickup device 22.

<Second Modification>

Next, a second modification of the first embodiment of the present invention will be described.

Figure 14:
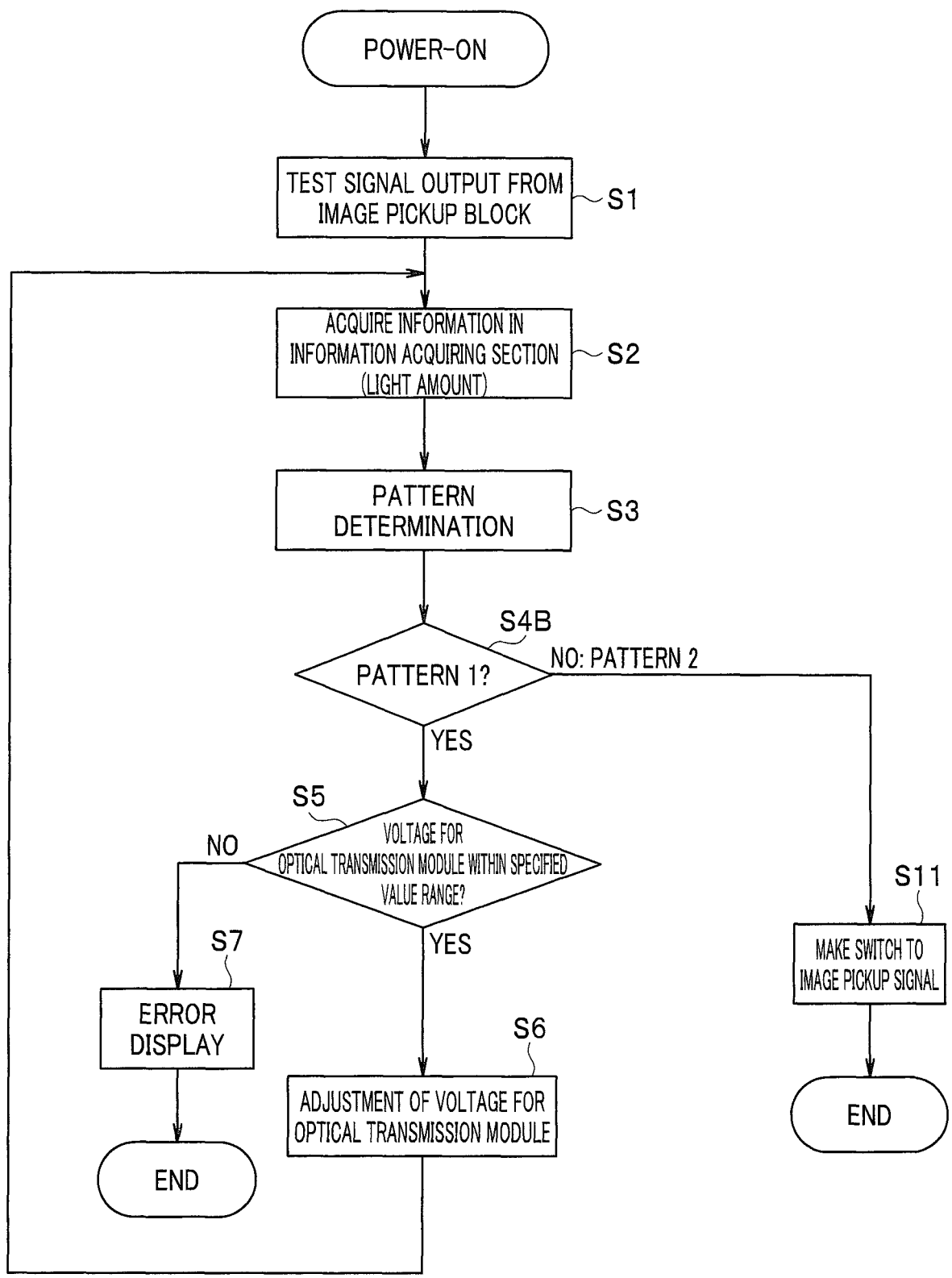
FIG. 14 is a flowchart illustrating a transmission quality control operation in the endoscope system according to the second modification of the first embodiment.
Figures 15, 16:
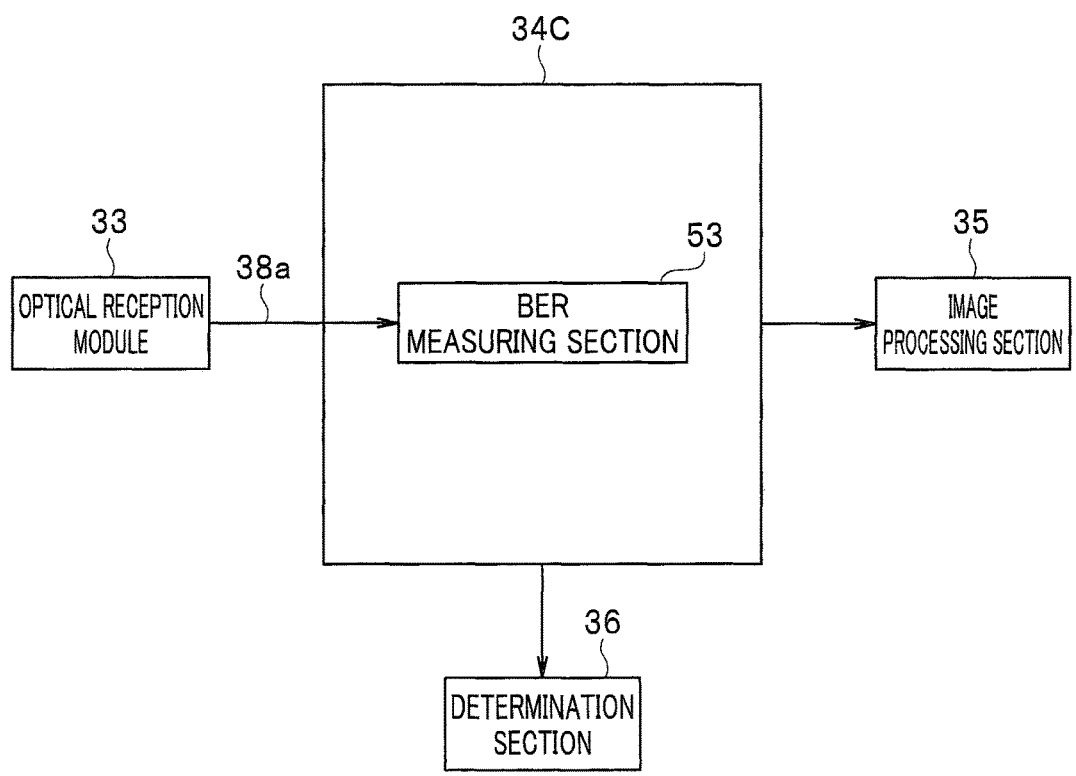
FIG. 15 is a table indicating processing performed by a determination section for each of patterns related to respective pieces of information acquired by an information acquiring section in the endoscope system according to the second modification of the first embodiment.
FIG. 16 is a block diagram illustrating a configuration of an information acquiring section in an endoscope system according to a third modification of the first embodiment.

FIG. 13 is a block diagram illustrating a configuration of an information acquiring section in an endoscope system according to a second modification of the first embodiment, FIG. 14 is a flowchart illustrating a transmission quality control operation in the endoscope system according to the second modification of the first embodiment, and FIG. 15 is a table indicating processing performed by a determination section for each of patterns related to respective pieces of information acquired by an information acquiring section in the endoscope system according to the second modification of the first embodiment.

The endoscope system according to the second modification is similar in basic configuration to the first embodiment but is only partially different in configuration of an information acquiring section 34B in a video processor 3 and in contents of measurement results used by a determination section 36 from the first embodiment. Therefore, here, only differences from the first embodiment will be described and description of parts in common with the first embodiment will be omitted.

As illustrated in FIG. 13, the information acquiring section 34B according to the second modification includes a light amount measuring section 52 connected to a second output wire 38b extending from an optical reception module 33.

As illustrated in FIG. 14, in the endoscope system 1 according to the second modification, as in the above, in step S1, a test signal is outputted from an image pickup block 21, and the test signal is converted into an optical signal by an optical transmission module 24 and then transmitted through optical fibers 25, an optical connector 26, an optical connector 31 and optical fibers 32 and then inputted to the optical reception module 33.

Also, in the second modification, a third electric signal outputted from the optical reception module 33, the third electric signal relating to a value of a light amount, is inputted to the light amount measuring section 52 in the information acquiring section 34B via the second output wire 38b. Then, the light amount measuring section 52 acquires light amount information based on the third electric signal (step S2), and outputs the acquired information to a determination section 36.

Subsequently, the determination section 36 determines a pattern related to the information acquired by the information acquiring section 34B, based on the information (light amount information) and determines whether transmission quality is good or poor according to a determination criterion (criterion value for satisfactory transmission quality) determined in advance for the information (step S3).

In other words, the determination section 36 controls related circuits to perform relevant processing according to the determined pattern (steps S4B to S7 or step S11).

Here, respective patterns and contents of respective types of processing for the patterns will be described with reference to FIG. 15. In FIG. 15, as in the first embodiment, marks "O" and "X " in the table indicates whether a determination criterion (criterion value for satisfactory transmission quality) for the relevant information is met or not.

In FIG. 15, the respective patterns (patterns 1 and 2) correspond to respective cases where the determination criterion is not met for the information and where the determination criterion is met for the information, and for the endoscope system according to the second modification, pattern 1: "light amount: poor", and
pattern 2: "light amount: good"
are specified.

Referring back to FIG. 14, in step S3, the determination section 36 determines the pattern according to the determination of whether the transmission quality is good or poor for the information (light amount) and if the pattern determined as a result is pattern 1 (step S4B), the determination section 36 proceeds to next step S5.

In steps S5 to S7 in the second modification, operation that is similar to the operation of the first embodiment is performed. More specifically, if the pattern determined by the determination section 36 is pattern 1: "light amount: poor", the power supply adjusting section 37 adjusts an input voltage to be applied to the optical transmission module 24 to be raised by unit of, for example, no more than 0.1 [V] and outputs the resulting input voltage to an input voltage supply line 27 in an endoscope 2 and the operation returns to step S2 above.

Subsequently, steps S2 to S6 above are repeated until the pattern becomes pattern 2: "light amount: good" as a result of the adjustment (control to raise the input voltage) by the power supply adjusting section 37.

Here, it is assumed that the input voltage is adjusted to be gradually raised by the adjustment by the power supply adjusting section 37 and reaches an upper limit value of a specified value range specified for the optical transmission module 24. If the pattern does not yet become pattern 2: "light amount: good" even in this case, it is determined as follows. In other words, it is determined in step S5 above that the input voltage falls outside the specified value range for the optical transmission module 24.

Therefore, as in the above, the determination section 36 proceeds to step S7 at this timing and error display is provided on a monitor 5 under the control of the determination section 36.

On the other hand, if the pattern determined in step S4B above is pattern 2: "light amount: good", it can be presumed that no problem occurs in both an optical signal transmission path and an image pickup device 22, and thus, the determination section 36 transmits a control signal indicating "initial setting completion" to the image pickup block 21 (step S11).

As described above, the second modification also enables achieving optical transmission that is consistently good in transmission quality in the optical signal transmission path even if transmission quality (for example, a light amount) deteriorates, and enables preventing transmission failure even if an amplitude of the relevant image pickup signal becomes small because of, e.g., operation failure in the image pickup device 22.

<Third Modification>

Next, a third modification of the first embodiment of the present invention will be described.

Figure 17:
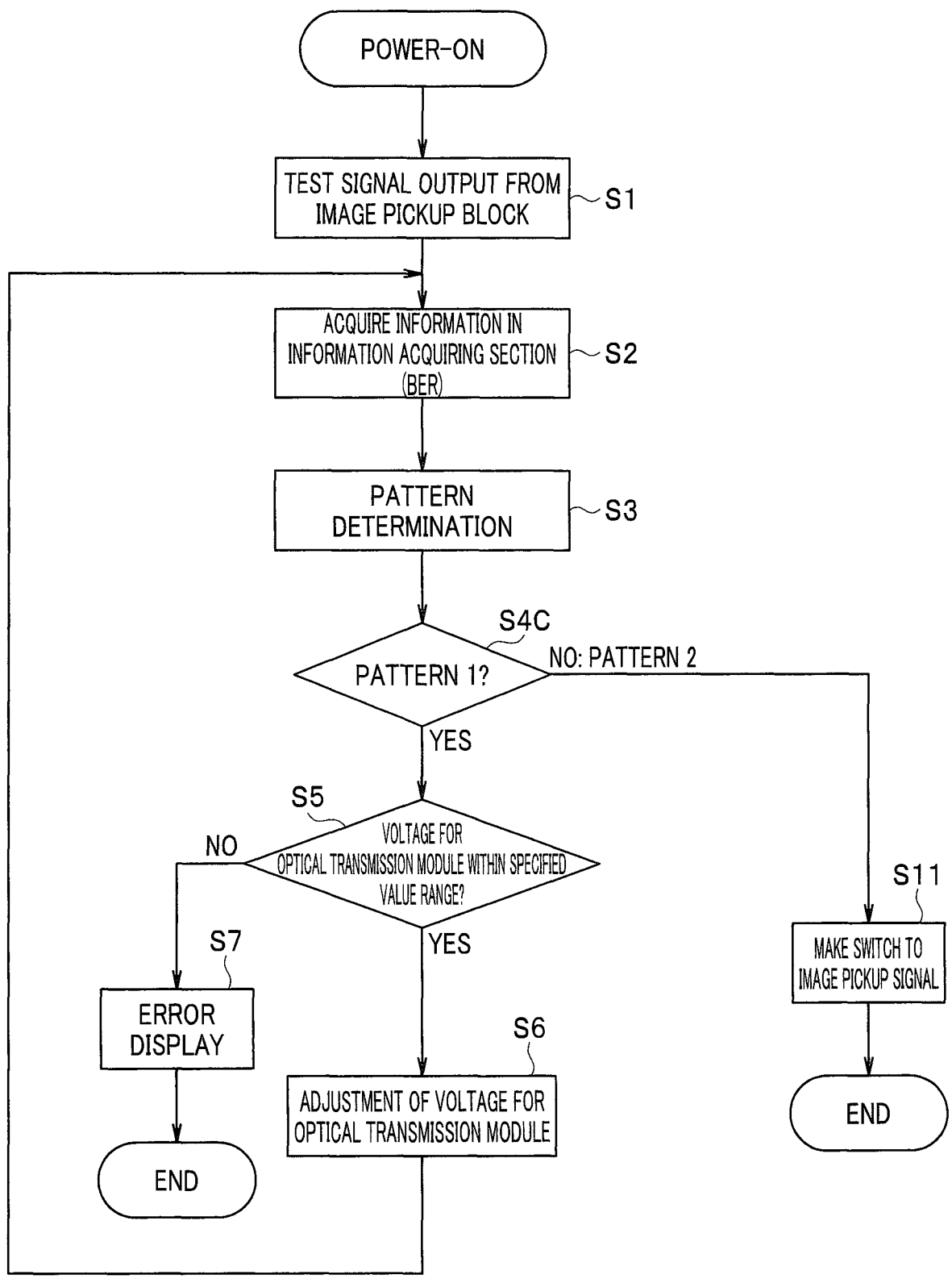
FIG. 17 is a flowchart illustrating a transmission quality control operation in the endoscope system according to the third modification of the first embodiment.
Figures 18, 19:
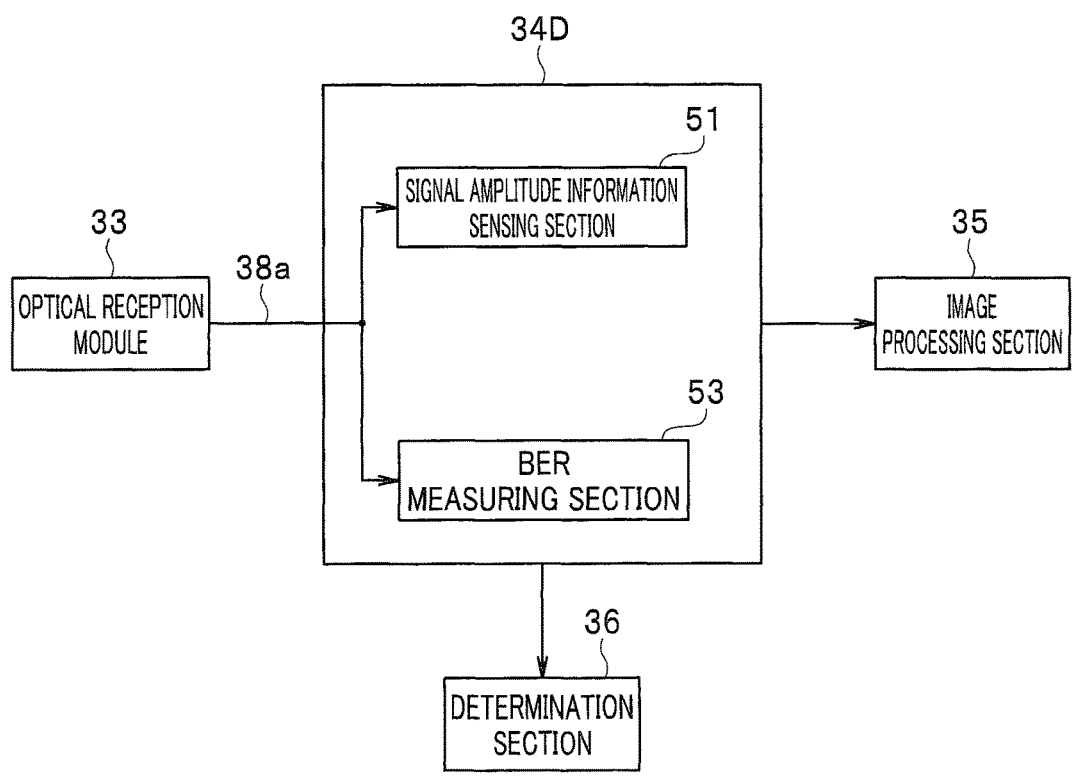
FIG. 18 is a table indicating processing performed by a determination section for each of patterns related to respective pieces of information acquired by an information acquiring section in the endoscope system according to the third modification of the first embodiment.
FIG. 19 is a block diagram illustrating a configuration of an information acquiring section in an endoscope system according to a fourth modification of the first embodiment.

FIG. 16 is a block diagram illustrating a configuration of an information acquiring section in an endoscope system according to a third modification of the first embodiment, FIG. 17 is a flowchart illustrating a transmission quality control operation in the endoscope system according to the third modification of the first embodiment, and FIG. 18 is a table indicating processing performed by a determination section for each of patterns related to respective pieces of information acquired by an information acquiring section in the endoscope system according to the third modification of the first embodiment.

The endoscope system according to the third modification is similar in basic configuration to the first embodiment but is only partially different in configuration of an information acquiring section 34C in a video processor 3 and in contents of measurement results used by a determination section 36 from the first embodiment.

Therefore, here, only differences from the first embodiment will be described and description of parts in common with the first embodiment will be omitted.

As illustrated in FIG. 16, the information acquiring section 34C according to the third modification includes a BER measuring section 53 connected to a first output wire 38a extending from an optical reception module 33.

As illustrated in FIG. 17, in the endoscope system 1 according to the third modification, as in the above, in step S1, a test signal is outputted from an image pickup block 21, and the test signal is converted into an optical signal by an optical transmission module 24 and then transmitted through optical fibers 25, an optical connector 26, an optical connector 31 and optical fibers 32 and then inputted to the optical reception module 33.

Also, in the third modification, a second electric signal outputted from the optical reception module 33 is inputted to the BER measuring section 53 in the information acquiring section 34C via the first output wire 38a. Then, the BER measuring section 53 measures a bit error rate (BER) of the optical signal based on the second electric signal to acquire BER information (step S2), and outputs the acquired information to the determination section 36.

Subsequently, the determination section 36 determines a pattern related to the information acquired by the information acquiring section 34C, based on the information (BER information) and determines whether transmission quality is good or poor according to a determination criterion (criterion value for satisfactory transmission quality) determined in advance for the information (step S3).

In other words, the determination section 36 controls related circuits to perform relevant processing according to the determined pattern (steps S4C to S7 or step S11).

Here, respective patterns and contents of respective types of processing for the patterns will be described with reference to FIG. 18. In FIG. 18, as in the first embodiment, marks "o" and "χ" in the table indicates whether a determination criterion (criterion value for satisfactory transmission quality) for the relevant information is met or not.

In FIG. 18, the respective patterns (patterns 1 and 2) correspond to respective cases where the determination criterion is not met for the information and where the determination criterion is met for the information, and for the endoscope system according to the third modification, pattern 1: "BER: poor", and
pattern 2: "BER: good"
are specified.

Referring back to FIG. 17, in step S3, the determination section 36 determines the pattern according to the determination of whether the transmission quality is good or poor for the information (BER) and if the pattern determined as a result is pattern 1 (step S4C), the determination section 36 proceeds to next step S5.

In steps S5 to S7 in the third modification, operation that is similar to the operation of the first embodiment is performed. More specifically, if the pattern determined by the determination section 36 is pattern 1: "BER: poor", the power supply adjusting section 37 adjusts an input voltage to be applied to the optical transmission module 24 to be raised by unit of, for example, no more than 0.1 [V] and outputs the resulting input voltage to an input voltage supply line 27 in an endoscope 2 and the operation returns to step S2 above.

Subsequently, steps S2 to S6 above are repeated until the pattern becomes pattern 2: "BER: good" as a result of the adjustment (control to raise the input voltage) by the power supply adjusting section 37.

Here, it is assumed that the input voltage is adjusted to be gradually raised by the adjustment by the power supply adjusting section 37 and reaches an upper limit value of a specified value range specified for the optical transmission module 24. If the pattern does not yet become pattern 2: "BER: good" even in this case, it is determined as follows. In other words, it is determined in step S5 above that the input voltage falls outside the specified value range for the optical transmission module 24.

Therefore, as in the above, the determination section 36 proceeds to step S7 at this timing and error display is provided on a monitor 5 under the control of the determination section 36.

Also, if the pattern determined in step S4C above is pattern 2: "BER: good", it can be presumed that no problem occurs in both an optical signal transmission path and an image pickup device 22, and thus, the determination section 36 transmits a control signal indicating "initial setting completion" to the image pickup block 21 (step S11).

As described above, the third modification also enables achieving optical transmission that is consistently good in transmission quality in the optical signal transmission path even if transmission quality (for example, BER) deteriorates, and enables preventing transmission failure even if an amplitude of the relevant image pickup signal becomes small because of, e.g., operation failure in the image pickup device 22.

<Fourth Modification>

Next, a fourth modification of the first embodiment of the present invention will be described.

Figure 20:
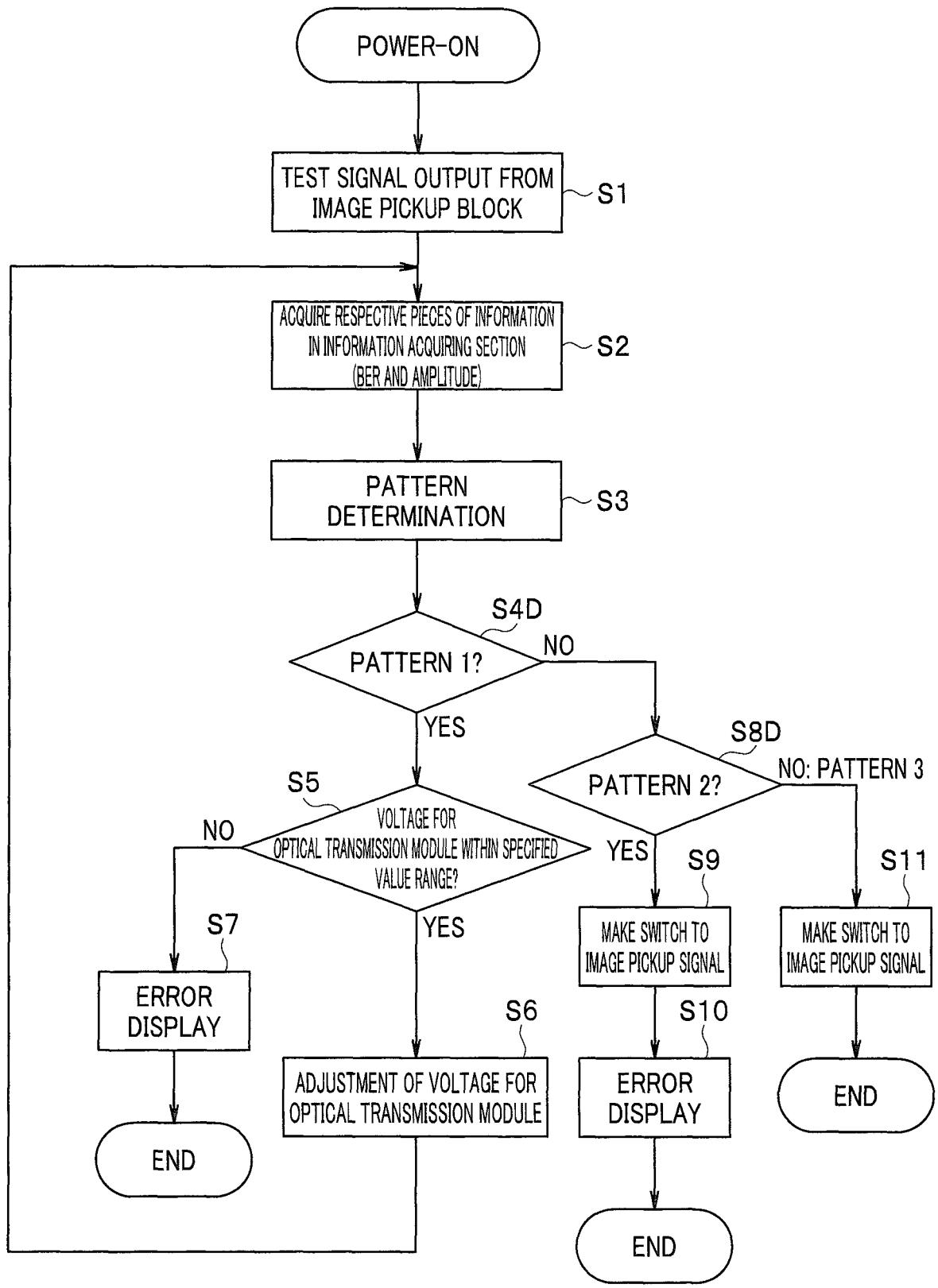
FIG. 20 is a flowchart illustrating a transmission quality control operation in the endoscope system according to the fourth modification of the first embodiment.

FIG. 19 is a block diagram illustrating a configuration of an information acquiring section in an endoscope system according to a fourth modification of the first embodiment, FIG. 20 is a flowchart illustrating a transmission quality control operation in the endoscope system according to the fourth modification of the first embodiment, and FIG. 21 is a table indicating processing performed by a determination section for each of patterns related to respective pieces of information acquired by an information acquiring section in the endoscope system according to the fourth modification of the first embodiment.

The endoscope system according to the fourth modification is similar in basic configuration to the first embodiment but is only partially different in configuration of an information acquiring section 34D in a video processor 3 and in contents of measurement results used by a determination section 36 from the first embodiment.

Therefore, here, only differences from the first embodiment will be described and description of parts in common with the first embodiment will be omitted.

As illustrated in FIG. 19, the information acquiring section 34D according to the fourth modification includes a signal amplitude information sensing section 51 and a BER measuring section 53 connected to a first output wire 38a extending from an optical reception module 33.

Also, as illustrated in FIG. 20, the endoscope system 1 according to the fourth modification, as in the above, in step S1, a test signal is outputted from an image pickup block 21, and the test signal is converted into an optical signal by an optical transmission module 24 and then transmitted through optical fibers 25, an optical connector 26, an optical connector 31 and optical fibers 32 and then inputted to the optical reception module 33.

The test signal converted into a second electric signal by the optical reception module 33 is inputted to the signal amplitude information sensing section 51 and the BER measuring section 53 in the information acquiring section 34D via the first output wire 38a.

Next, the respective sections (the signal amplitude information sensing section 51 and the BER measuring section 53) in the information acquiring section 34D acquire amplitude information and BER information, respectively, based on the test signal that is the second electric signal (step S2), and output the respective acquired pieces of information to the determination section 36.

Subsequently, the determination section 36 determines a pattern related to the pieces of information acquired by the information acquiring section 34D, based on the pieces of information (the amplitude information and the BER information) and determines whether transmission quality is good or poor according to determination criterion (criterion values for satisfactory transmission quality) determined in advance for the respective pieces of information (step S3).

Subsequently, the determination section 36 controls related circuits to perform relevant processing according to the determined pattern (steps S4D to S7 or step S11).

Here, respective patterns and contents of respective types of processing for the patterns will be described with reference to FIG. 21. In FIG. 21, as in the first embodiment, marks "o" and "χ" in the table indicates whether a determination criterion (criterion value for satisfactory transmission quality) for the relevant piece of information is met or not.

In FIG. 21, the respective patterns (patterns 1 to 3) correspond to respective types of combination of "good" and/or "poor" for the determination criterions for respective pieces of information, and for the endoscope system according to the fourth modification, the respective patterns indicated below are specified.

pattern 1: combination of "BER: poor" and "amplitude: good", pattern 2: combination of "BER: good" and "amplitude: poor", and pattern 3: combination of "BER: good" and "amplitude: good".

Referring back to FIG. 20, in step S3, the determination section 36 determines the pattern according to the determination of whether the transmission quality is good or poor for each of the pieces of information and if the pattern determined as a result is pattern 1 (step S4D), the determination section 36 proceeds to next step S5.

In steps S5 to S7 in the fourth modification, operation that is similar to the operation of the first embodiment is performed. More specifically, the pattern determined by the determination section 36 is pattern 1: "BER: poor" and "amplitude: good", the power supply adjusting section 37 adjusts an input voltage to be applied to the optical transmission module 24 to be raised by unit of, for example, no more than 0.1 [V] and outputs the resulting input voltage to an input voltage supply line 27 in an endoscope 2 and the operation returns to step S2 above.

Subsequently, steps S2 to S6 above are repeated until the pattern becomes pattern 2 or pattern 3 as a result of adjustment (control to raise the input voltage or control to lower the input voltage) by the power supply adjusting section 37.

Here, it is assumed that the input voltage is adjusted to be gradually raised by the adjustment by the power supply adjusting section 37 and reaches an upper limit value of a specified value range specified for the optical transmission module 24. If the pattern yet becomes neither pattern 2 nor pattern 3 even in this case, it is determined in step S5 above that the input voltage falls outside the specified value range for the optical transmission module 24.

Therefore, as in the above, the determination section 36 proceeds to step S7 at this timing and error display is provided on a monitor 5 under the control of the determination section 36.

On the other hand, if the pattern determined in step S4D above is pattern 2 or pattern 3, the determination section 36 proceeds to step S8D. Then, in step S8D, the determination section 36 determines whether the pattern is either pattern 2 or pattern 3 (step S8D).

Here, if the pattern is pattern 2, that is, pattern 2: combination of "BER: good" and "amplitude: poor", the "BER" is "good" but the "amplitude" is "poor", and thus, it can be presumed that no problem occurs in an optical signal transmission path but some problem occurs in an image pickup device 22 itself.

Therefore, the determination section 36 transmits a control signal indicating "initial setting completion" to the image pickup block 21 in order to switch the test signal outputted from the image pickup block 21 to an image pickup signal (step S9). Also, concurrently, the determination section 36 regards a failure as occurring in the image pickup device 22 and controls respective related circuits to provide predetermined error display on the monitor 5 (step S10).

On the other hand, if the pattern is pattern 3 in step S8D, that is, pattern 3: combination of "BER: good" and "amplitude: good", since it can be presumed that no problem occurs in both the optical signal transmission path and the image pickup device 22, the determination section 36 transmits a control signal indicating "initial setting completion" to the image pickup block 21 (step S11).

As described above, the fourth modification also enables achieving optical transmission that is consistently good in transmission quality in the optical signal transmission path even if transmission quality (for example, an amplitude and/or jitter) deteriorates, and enables preventing transmission failure even if an amplitude of the relevant image pickup signal becomes small because of, e.g., operation failure in the image pickup device 22.

Second Embodiment

Next, a second embodiment of the present invention will be described.

Figure 22:
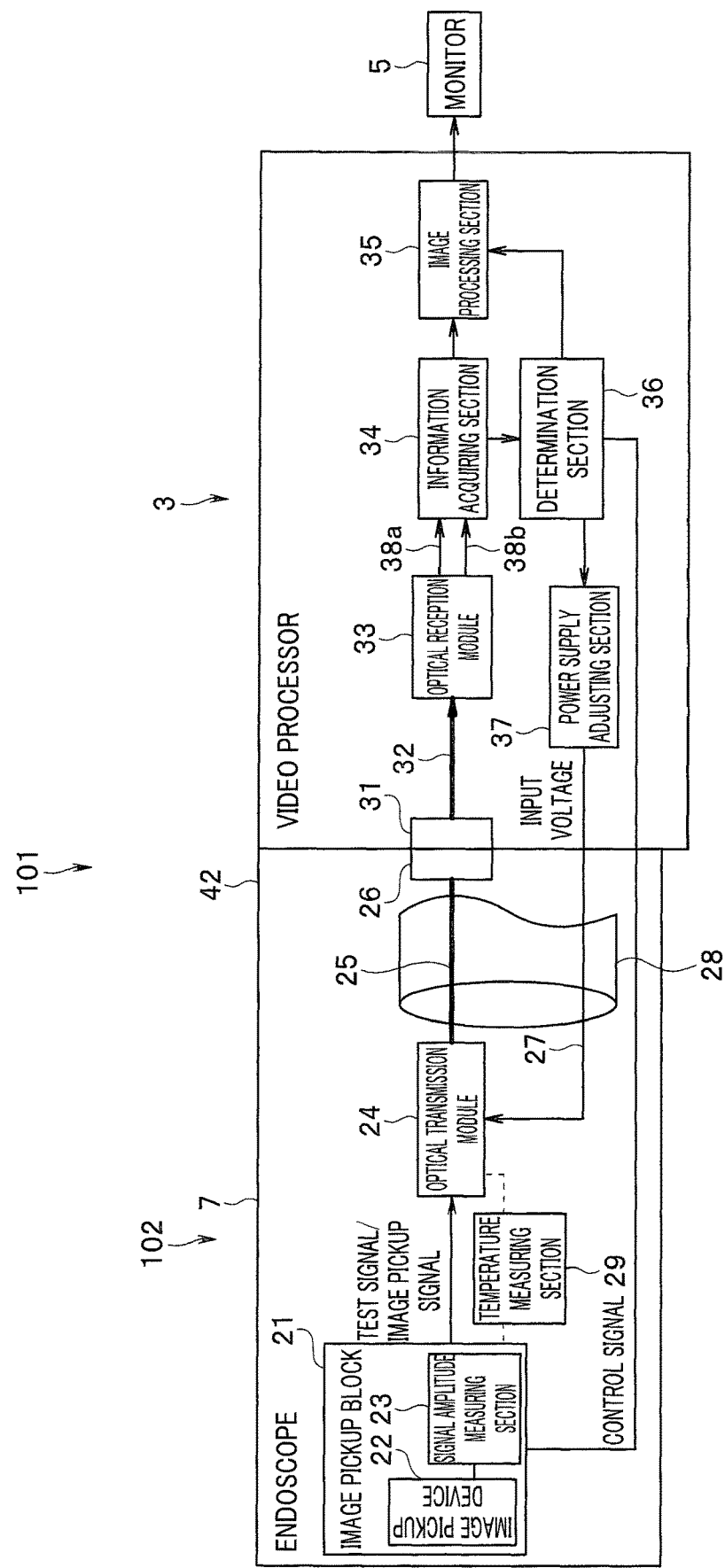
FIG. 22 is a block diagram illustrating an electric configuration of an endoscope system according to a second embodiment of the present invention.
Figure 23:
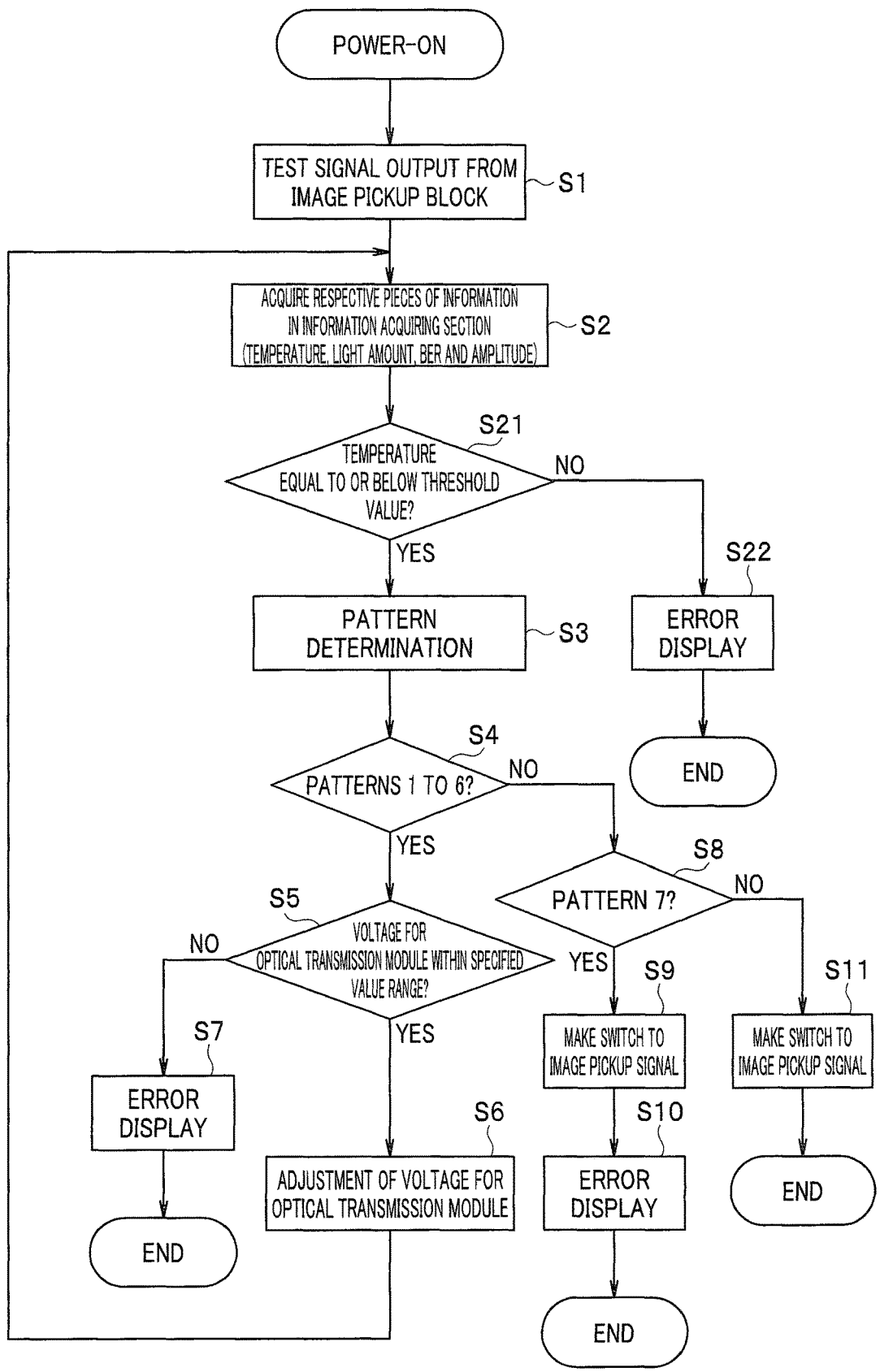
FIG. 23 is a flowchart illustrating a transmission quality control operation in the endoscope system according to the second embodiment.

FIG. 22 is a block diagram illustrating an electric configuration of an endoscope system according to a second embodiment of the present invention and FIG. 23 is a flowchart illustrating a transmission quality control operation in the endoscope system according to the second embodiment.

An endoscope system 101 according to the second embodiment is similar in basic configuration to the first embodiment but additionally includes a temperature measuring section configured to measure a temperature of an image pickup device or an optical transmission module in an endoscope.

Therefore, here, only differences from the first embodiment will be described and description of parts in common with the first embodiment will be omitted.

As illustrated in FIGS. 22 and 23, in the endoscope system 101 according to the second embodiment, an endoscope 102 includes a temperature measuring section 29 disposed in a distal end portion 7 of an insertion portion 6, the temperature measuring section 29 being configured to measure a temperature of an image pickup device 22 or an optical transmission module 24.

As in the first embodiment, information of the temperature of the image pickup device 22 or the optical transmission module 24 measured by the temperature measuring section 29 which is a temperature measuring apparatus is added to an image pickup signal or a test signal outputted from an image pickup block 21.

Then, as in the first embodiment, the test signal or the image pickup signal with the temperature information added is converted into an optical signal by the optical transmission module 24 and then inputted to an optical reception module 33 through optical fibers 25 and optical fibers 32.

Subsequently, the test signal or the image pickup signal, with the temperature information added, inputted to the optical reception module 33 is inputted to an information acquiring section 34, and the information acquiring section 34 acquires the temperature information together with amplitude information, light amount information and BER information, which have been described above (see step S2 in FIG. 23).

Furthermore, the temperature information acquired by the information acquiring section 34 is sent out to a determination section 36, and the determination section 36 performs determination on the temperature of the image pickup device 22 or the optical transmission module 24 (see step S21 in FIG. 23).

In step S21, if the determination section 36 determines that the temperature of the image pickup device 22 or the optical transmission module 24 is equal to or below a predetermined threshold value, as illustrated in FIG. 23, control that is similar to the control in steps S4 to S11 (see FIG. 4) in the first embodiment is performed.

On the other hand, in step S21, if the determination section 36 determines that the temperature of the image pickup device 22 or the optical transmission module 24 exceeds the predetermined threshold value, as illustrated in FIG. 23, the determination section 36 controls related circuits to provide predetermined error display (step S22).

As described above, the endoscope system according to the second embodiment exerts an effect of preventing a patient and/or a surgeon from suffering burn injury owing to an increase in temperature around the image pickup device 22, that is, temperature of the distal end portion of the insertion portion of the endoscope, by measuring the temperature of the image pickup device 22 or the optical transmission module 24, in addition to the transmission quality maintenance effect according to the first embodiment.

The present invention is independently of the above-described embodiments and various changes, alterations and the like are possible without departing from the spirit of the present invention.

The present invention enables provision of an endoscope system employing an optical signal transmission method, the endoscope system preventing a transmission failure and consistently providing optimum transmission quality.

What is claimed is:

1. An endoscope system comprising:
an endoscope configured to pick up an image of a subject, and
a video processor to which the endoscope is connectable, wherein the endoscope comprising:
an image pickup sensor configured to pick up an image of the subject and output at least a predetermined first electric signal,
an optical transmission module including a light emitting element configured to be driven by a predetermined applied voltage and convert the first electric signal from the image pickup sensor into an optical signal and output the optical signal,
an optical fiber configured to transmit the optical signal outputted from the optical transmission module, and
a signal amplitude measuring circuit configured to measure a signal amplitude of the first electric signal and add signal amplitude information that is a result of the measurement to the first electric signal; and
the video processor is configured to:
receive the optical signal transmitted from the optical fiber and convert the optical signal into a predetermined second electric signal and output the predetermined second electric signal, and output a third electric signal according to a light amount of the optical signal;
sense the signal amplitude information based on the second electric signal, measure a bit error rate of the optical signal based on the second electric signal, and measure a light amount of the optical signal based on the third electric signal;
determine a transmission state of the optical signal based on the transmission information relating to the signal amplitude information, the light amount and the bit error rate, and
adjust the applied voltage according to a result of the determination and output the applied voltage.

2. The endoscope system according to claim 1, wherein the first electric signal is a test signal outputted from the image pickup sensor during a period until an image pickup signal relating to the subject is outputted, after activation of the image pickup sensor.

3. The endoscope system according to claim 1, wherein the first electric signal is an image pickup signal outputted from the image pickup sensor.

4. An endoscope system comprising:
an endoscope configured to pick up an image of a subject, and
a video processor to which the endoscope is connectable, wherein the endoscope comprising:
an image pickup sensor configured to pick up an image of the subject and output at least a predetermined first electric signal;
an optical transmission module including a light emitting element configured to be driven by a predetermined applied voltage and convert the first electric signal from the image pickup sensor into an optical signal and output the optical signal;
an optical fiber configured to transmit the optical signal outputted from the optical transmission module; and
a signal amplitude measuring circuit configured to measure a signal amplitude of the first electric signal and add signal amplitude information that is a result of the measurement to the first electric signal; and
the video processor is configured to:
receive the optical signal transmitted from the optical fiber and convert the optical signal into a predetermined second electric signal and output the predetermined second electric signal, and output a third electric signal according to a light amount of the optical signal;
sense the signal amplitude information based on the second electric signal and measure a bit error rate of the optical signal based on the second electric signal;
determine the transmission state of the optical signal based on transmission information relating to the signal amplitude information and the bit error rate; and
adjust the applied voltage according to a result of the determination and output the applied voltage.

5. The endoscope system according to claim 1, the video processor is further configured to monitor whether or not a value of the applied voltage is within a predetermined specified value range.

6. The endoscope system according to claim 1, further comprising a display configured to display the transmission state.

7. The endoscope system according to claim 1, wherein:
the endoscope is configured to measure a temperature of the image pickup sensor or the optical transmission module;
the video processor is further configured to acquire temperature information relating to the temperature of the image pickup sensor or the optical transmission module; and determine whether or not an endoscopic examination can be performed based on the acquired temperature information.

* * * * *